United States Patent
Jermy et al.

(10) Patent No.: US 12,102,651 B1
(45) Date of Patent: *Oct. 1, 2024

(54) SOLVENT-BASED METHOD FOR MAKING NANOCOMPOSITE PHARMACEUTICAL MATERIAL

(71) Applicant: Imam Abdulrahman Bin Faisal University, Dammam (SA)

(72) Inventors: B. Rabindran Jermy, Dammam (SA); Vijaya Ravinayagam, Dammam (SA); Suriya Rehman, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 0 days.

This patent is subject to a terminal disclaimer.

(21) Appl. No.: 18/739,378

(22) Filed: Jun. 11, 2024

Related U.S. Application Data

(60) Continuation of application No. 18/295,863, filed on Apr. 5, 2023, now Pat. No. 12,029,758, which is a
(Continued)

(51) Int. Cl.
*A61K 33/38* (2006.01)
*A61K 33/243* (2019.01)
(Continued)

(52) U.S. Cl.
CPC ............ *A61K 33/38* (2013.01); *A61K 33/243* (2019.01); *A61K 47/02* (2013.01); *A61P 31/04* (2018.01)

(58) Field of Classification Search
CPC ...... A61K 33/38; A61K 33/243; A61K 47/02; A61P 31/04
See application file for complete search history.

(56) References Cited

U.S. PATENT DOCUMENTS

| 11,850,260 B2 | 12/2023 | Jermy | |
| 12,029,758 B2 * | 7/2024 | Jermy | ................ A61K 33/243 |

(Continued)

FOREIGN PATENT DOCUMENTS

| EP | 0 106 674 A2 | 4/1984 |
| EP | 1 931 465 B1 | 4/2016 |

(Continued)

OTHER PUBLICATIONS

M. Amina, et al., "Prospective of biosynthesized *L. satiVum* oil/PEG/Ag-MgO bionanocomposite film for its antibacterial and anticancer potential", Saudi Journal of Biological Sciences, vol. 28, Issue 10, Oct. 2021, pp. 5971-5985.
(Continued)

*Primary Examiner* — Ernst V Arnold
(74) *Attorney, Agent, or Firm* — Oblon, McClelland, Maier & Neustadt, L.L.P.

(57) ABSTRACT

A medicinal nanocomposite is provided. The medicinal nanocomposite includes 80 to 99 wt. % carrier particles of a porous silicate material selected from a group including mesoporous silica, silicalite, mesosilicalite, silver-incorporated silicalite, and silver-incorporated mesosilicalite, the carrier particles comprising a pore framework, 0.5 to 10 wt. % silver nanoparticles (Ag NPs) disposed the pore framework, and 0.5 to 10 wt. % of a platinum-containing pharmaceutical compound disposed on at least one surface selected from an interior pore surface of the carrier particles, an exterior surface of the carrier particles, and a surface of the silver nanoparticles. The medicinal nanocomposite releases less than 10 mole % of the platinum-containing pharmaceutical compound after 60 to 84 hours at a pH of 4.5 to 7, based on an initial amount of the platinum-containing pharmaceutical compound present in the medicinal nanocomposite.

15 Claims, 30 Drawing Sheets

Related U.S. Application Data division of application No. 17/665,014, filed on Feb. 4, 2022, now Pat. No. 11,850,260.

(51) Int. Cl.
*A61K 47/02* (2006.01)
*A61P 31/04* (2006.01)

(56) References Cited

U.S. PATENT DOCUMENTS

| | | |
|---|---|---|
| 2015/0018486 A1 | 1/2015 | Tamarkin et al. |
| 2018/0028686 A1 | 2/2018 | Brinker et al. |
| 2020/0163899 A1 | 5/2020 | Fernandes et al. |

FOREIGN PATENT DOCUMENTS

| | | |
|---|---|---|
| JP | 2021-518376 A | 8/2021 |
| WO | WO 2020/172618 A2 | 8/2020 |

OTHER PUBLICATIONS

Han Wang, et al., "Scintillator-Based Nanohybrids with Sacrificial Electron Prodrug for Enhanced X-ray-Induced Photodynamic Therapy", NANO Letters, vol. 18, No. 9, Jul. 27, 2018, pp. 5768-5774 (Abstract only).

Kasirajan Kasinathan, et al., "Fabrication of eco-friendly chitosan functionalized few-layered $WS_2$ nanocomposite implanted with ruthenium nanoparticles for in vitro antibacterial and anticancer activity: Synthesis, characterization, and pharmaceutical applications", International Journal of Biological Macromolecules, vol. 190, Nov. 1, 2021, pp. 520-532 (Abstract only).

\* cited by examiner

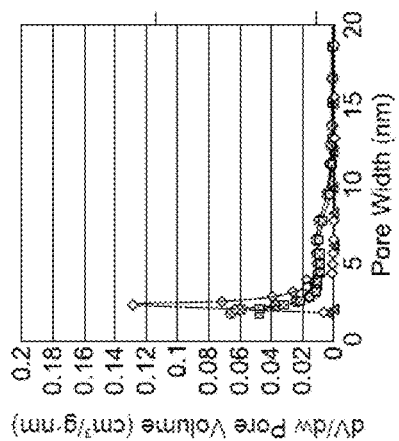
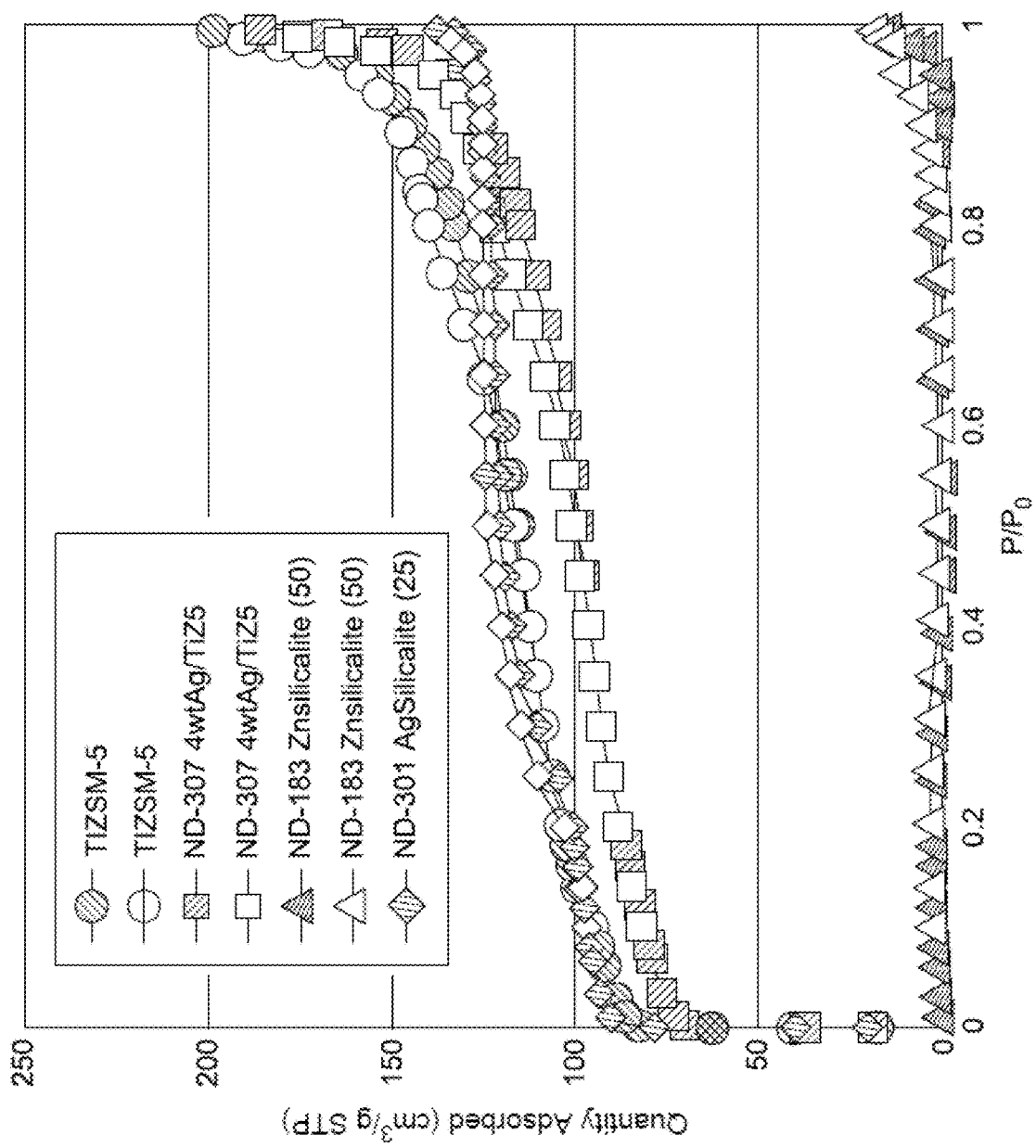
FIG. 9B
FIG. 9A

SOLVENT-BASED METHOD FOR MAKING NANOCOMPOSITE PHARMACEUTICAL MATERIAL

CROSS-REFERENCE TO RELATED APPLICATIONS

The present application is a Continuation of U.S. application Ser. No. 18/295,863, now allowed, having a filing date of Apr. 5, 2023 which is a Continuation of U.S. application Ser. No. 17/665,014, now U.S. Pat. No. 11,850,260, having a filing date of Feb. 4, 2022.

BACKGROUND

Technical Field

The present disclosure is directed to a medicinal nanocomposite, and a method of forming the medicinal nanocomposite for treating cervical and colorectal cancers and fighting against bacterial infections.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

Treatments for cancers such as cervical cancer and colorectal cancer may include surgery, radiation therapy, chemotherapy, or targeted therapy. However, a continued high mortality of cancer patients reveals shortcomings of such treatments. Also, during cancer treatment, the immunity of the patient is compromised and as a result, the patient is more susceptible to bacterial infections. Conventionally, pharmaceutical compositions are used for cancer and microbial treatments. However, conventional compositions suffer from drawbacks such as poor selectivity between cancerous and non-cancerous cells.

In recent years metal complexes are being increasingly used as drugs for selective delivery of the drug to cancerous and bacterial cells. However, an excessive concentration of metal ions in the patient affects non-cancerous cells and causes drug induced toxicity. Hence, delivery of agents capable of inducing toxicity to cancerous cells while preventing the non-cancerous cells from the adverse effects of metal complexes, is highly desirable. Furthermore, the conventional treatment methods include administration of multiple drugs to treat secondary infections like bacterial infections, that are commonly encountered among cancer patients. Therefore, there is a need of an efficient composition which may substantially reduce or eliminate the above limitations.

SUMMARY

The present disclosure relates to a medicinal nanocomposite. The medicinal nanocomposite includes 80 to 99 wt. % carrier particles of a porous silicate material selected from a group including mesoporous silica, silicalite, mesosilicalite, silver-incorporated silicalite, and silver-incorporated mesosilicalite, the carrier particles comprising a pore framework. The medicinal nanocomposite further includes 0.5 to 10 wt. % silver nanoparticles (Ag NPs) dispersed the pore framework. The silver nanoparticles are distinct from silver present in the silver-incorporated silicalite and/or silver-incorporated mesosilicalite. Furthermore, the medicinal nanocomposite includes 0.5 to 10 wt. % of a platinum-containing pharmaceutical compound disposed on at least one surface selected from an interior pore surface of the carrier particles, an exterior surface of the carrier particles, and a surface of the silver nanoparticles. The medicinal nanocomposite releases less than 10 mole percent (mol. %) of the platinum-containing pharmaceutical compound after 60 to 84 hours at a pH of 4.5 to 7, based on an initial amount of the platinum-containing pharmaceutical compound present in the medicinal nanocomposite.

In some embodiments, the carrier particles are particles of mesoporous silica which are substantially spherical and have a mean particle size of 50 to 110 nanometers (nm).

In some embodiments, the carrier particles are particles of mesoporous silica which are amorphous by powder X-ray diffraction (PXRD).

In some embodiments, the particles are particles of a porous silicate material selected from a group including silicalite, mesosilicalite, silver-incorporated silicalite, and silver-incorporated mesosilicalite with a mean particle size of 25 to 400 nm.

In some embodiments, the carrier particles are particles of silver-incorporated mesosilicalite that have a silicon to silver mole ratio of 10:1 to 150:1.

In some embodiments, the carrier particles are particles of silver-incorporated silicalite with a silicon to silver mole ratio of 10:1 to 150:1.

In some embodiments, the silver nanoparticles are disposed on an interior pore surface of the carrier particles and/or an exterior surface of the carrier particles and have a mean particle size of 5 to 50 nm.

In some embodiments, the silver nanoparticles are crystalline by PXRD.

In some embodiments, the platinum-containing pharmaceutical compound is at least one selected from a group including cisplatin, oxaliplatin, and carboplatin.

In some embodiments, the medicinal nanocomposite has a mean pore size of 15 to 27.5 nm, a mean pore volume of 0.05 to 0.35 cubic centimeter per gram ($cm^3/g$), and a mean surface area of 7.5-75-meter square per gram ($m^2/g$).

In some embodiments, a coated nanocomposite includes 80 to 99 wt. % of the medicinal nanocomposite of the present disclosure and 1 to 20 wt. % of a biocompatible coating. The biocompatible coating comprises at least one selected from a group consisting of polyethylene glycol, polypropylene glycol, polylactic acid, polyvinyl alcohol, polyvinyl pyrrolidone, alginate, chitosan, dextran, and hyaluronic acid.

In another exemplary embodiment, a method of forming the medicinal nanocomposite is described. The method includes aging a reaction mixture including a silver source and particles of the porous silicate material in a first solvent for 4 to 24 hours to form an aged mixture. The method further includes heating the aged mixture to 90 to 150 degrees Celsius (C) for 2 to 12 hours to form a first product; and calcining the first product at 350 to 650° C. for 1 to 6 hours to form a second product. The method further includes mixing the second product and the platinum-containing pharmaceutical compound in a second solvent for 2 to 12 hours at −15 to 15° C. to form the medicinal nanocomposite; followed by isolating the medicinal nanocomposite.

In some embodiments, the silver source is silver nitrate.

In some embodiments, the first solvent is water and the second solvent is a normal saline solution.

In some embodiments, the porous silicate material is selected from the group including silver-incorporated silicalite and silver-incorporated mesosilicalite. The porous silicate material may be prepared by adding a suspension of colloidal silica in a first solvent to a basic solution including 2 to 3 Molar (M) hydroxide base to form a raw silicate solution. The method further includes aging the raw silicate solution for 1 to 30 minutes to form an aged silicate solution; adding a silver source to the aged silicate solution to form a first reaction mixture; and aging the first reaction mixture to form an aged reaction mixture. The method further includes adding a template selected from a group including tetrapropyl ammonium hydroxide and Cetyltrimethylammonium bromide to the aged reaction mixture to form a templated solution. The method further includes stirring the templated solution for 0.5 to 3 hours to form a second reaction mixture. The method further includes hydrothermally treating the second reaction mixture at 125 to 195° C. for 24 to 120 hours to form a first precipitate. The method further includes calcining the first precipitate at 400 to 750° C. for 2 to 12 hours to form the porous silicate material.

In some embodiments, the template is tetrapropyl ammonium hydroxide, and the porous silicate material is silver-incorporated silicalite.

In some embodiments, the template is cetyltrimethylammonium bromide, and the porous silicate material is silver-incorporated mesosilicalite.

In some embodiments, a method of treating cervical cancer, colorectal cancer, or both in a subject includes administering to the subject an effective amount of the medicinal nanocomposite.

In some embodiments, an antibacterial composition includes the medicinal nanocomposite, the antibacterial composition having a minimum inhibitory concentration (MIC) of 0.1 to 3.5 milligram per milliliter (mg/ml) against a bacterial strain selected from a group including *Pseudomonas aeruginosa* and *Staphylococcus aureus*.

In some embodiments, a method of treating a bacterial infection in a subject includes administering to the subject an effective amount of the antibacterial composition.

The foregoing general description of the illustrative present disclosure and the following detailed description thereof are merely exemplary aspects of the teachings of the present disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein:

FIG. 9A depicts $N_2$ adsorption isotherm of TiZSM-5, 4 wt. % Ag/TiZSM-5, Zn-silicalite, and Ag-silicalite, according to certain embodiments.

FIG. 9B depicts a plot of pore size calculated from the $N_2$ adsorption isotherms shown in FIG. 9A.

DETAILED DESCRIPTION

Figure 1:
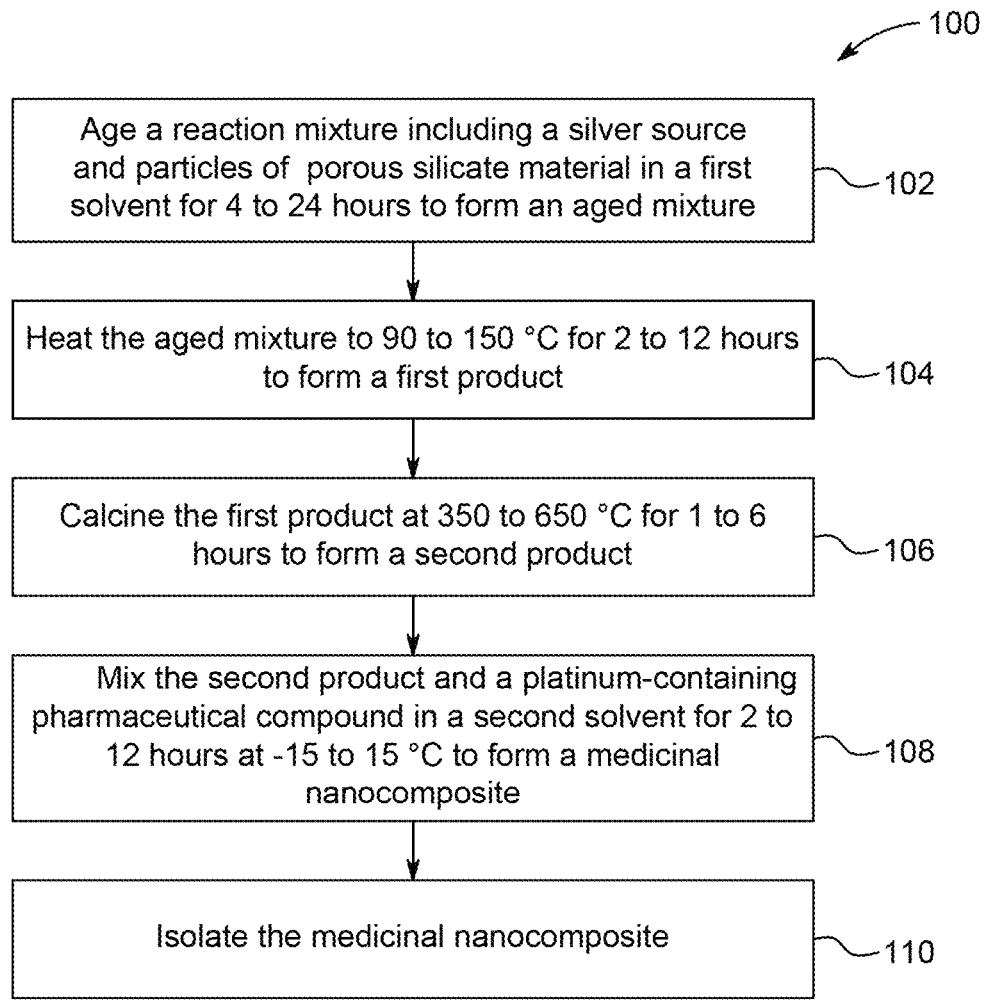
FIG. 1 is a schematic flow diagram of a method of forming a medicinal nanocomposite, according to certain embodiments.

In the drawings, like reference numerals designate identical or corresponding parts throughout the several views. Further, as used herein, the words "a," "an" and the like generally carry a meaning of "one or more," unless stated otherwise.

Furthermore, the terms "approximately," "approximate," "about," and similar terms generally refer to ranges that include the identified value within a margin of 20%, 10%, or preferably 5%, and any values there between.

Embodiments of the present disclosure are directed to a method for making a medicinal nanocomposite. The medicinal nanocomposite of the present disclosure is effective in treatment of cancers and bacterial infections. Although the description herein refers to the use of the medicinal nanocomposite for treatment of cervical and colon cancers, it may be understood by a person skilled in the art that aspects of the present disclosure may be directed towards treatment of other cancers such as cancer of thyroid, endocrine system, brain, breast, cervix, ovary, sarcoma, stomach, uterus medulloblastoma, colon, head and neck, liver, kidney, lung, non-small cell lung, melanoma, mesothelioma, or pancreatic cancer.

The medicinal nanocomposite comprises 80 to 99 weight percent (wt. %), preferably 81 to 98.5 wt %, preferably 82 to 98 wt. %, preferably 83 to 97.5 wt.5, preferably 85 to 97 wt. %, preferably 86 to 96.5 wt. %, preferably 87 to 96 wt. %, preferably 87.5 to 95.5 wt. %, preferably 88 to 95 wt. %, preferably 88.5 to 94.5 wt. %, preferably 89 to 94 wt. % carrier particles. The carrier particles comprise a porous silicate material selected from a group consisting of mesoporous silica, silicalite, mesosilicalite, silver-incorporated silicalite, and silver-incorporated mesosilicalite. The carrier particles comprise a pore framework. In some embodiments, this framework comprises both micropores and mesopores.

Silicalite is a polymorph of silica having a structure analogous to zeolite. The term "mesosilicalite" may be used to refer to any silicalite material which contains mesopores. The term "hierarchical silicalite" is used to indicate a silicalite which has at least two types of pore systems with different pore size ranges. For example, a hierarchical silicalite may have a pore size range in the micropore range and a pore size range in the mesopore range. Such a material may be classified as both a mesosilicalite and a hierarchical silicalite. In some embodiments, a hierarchical silicalite includes mesopores of a hexagonal structure and micropores. In some embodiments, the micropores have a microporous volume in the range of 0.05 cc/g to 0.1 cc/g, 0.06 cc/g to 0.09 cc/g, or 0.07 cc/g to 0.08 cc/g. U.S. patent application Ser. No. 15/478,794 which published as US 2018/0280303—incorporated herein by reference in its entirety, discloses the synthesis of an exemplary silicalite having a particle size in the range of 1 to 5 nm using Ludox® AS-40 and tetrapropylammonium bromide (TPABr) as silica and templating agent, respectively. In embodiments where the porous silicate matrix is mesosilicalite, the carrier particles may be referred to as a "mesosilicalite carrier particles".

The hexagonal structure of silicalite and mesosilicalite may be described as well-ordered and comparable in structure to MCM-41 mesoporous material as described by Kresge et al. (1992), Sayari, et al. (1996), and Moller, et al. (2013) [Kresge C T, Leonowicz M E, Roth W J, Vartuli J C, Beck J S, Nature 359 (1992) 710-712; 15; A. Sayari, Chem. Mater. 8 (1996) 1840-1852; and K. Moller, T. Bein, Chem. Soc. Rev., 42 (2013) 3689, each incorporated herein in their entirety]. MCM-41 (Mobil Composition of Matter No. 41) is a mesoporous silica material with a hierarchical structure from a family of silicate and aluminosilicate solids that were developed by researchers at Mobil Oil Corporation and that can be used as catalysts or catalyst supports. MCM-41 and MCM-48 both comprise an amorphous silica wall and possess long range ordered framework with uniform mesopores. These materials also possess large surface area, which can be up to more than 1,000 $m^2g^{-1}$. The pore diameter of these materials can be controlled to fall within a mesoporous range between 1.5 and 20 nm by adjusting the synthesis conditions and/or by employing surfactants with different chain lengths in their preparation. In some embodiments, the mesopores and micropores of the porous silicate material characterize the hierarchical structure of the silicalite, wherein the mesopores form the mesophase and the micropores form the microphase. The relative weight ratios of these two phases approximate the relative weight ratios of the SiMCM-41 and silicalite used in the synthesis.

In some embodiments, the hierarchy of the mesophase and microphase in hierarchical silicalite results in improved interaction with materials that can be carried, adsorbed, absorbed and/or otherwise contacted by the porous silicate matrix due to a greater surface area of contact with two phases instead of one phase, and an improved flow, or exchange, of the materials that may be carried into and out of the porous silicate matrix. The presence of micropores and mesopores in the porous silicate matrix may exhibit a unique hysteresis pattern. The pore size distribution of the silicalite typically exhibits two types of pores between 2.4 nm and 3.7 nm, while Q-10 silica and SiMCM-41 each show one type of pore at 15 nm and 2.9 nm, respectively.

The porous silicate matrix may comprise two types of materials, a first material having 2D properties and a second material having 3D properties. The first material may be layered under the second material, thus forming a hierarchically structured nanocarrier. In some such embodiments, the amount of mesophase and microphase is calculated based on the weight percentage of composite SiMCM-41/silicalite in comparison to parent silicalite and SiMCM-41. Alternatively, a calibration curve may be constructed from the X-Ray diffraction spectra of mesosilicalite nanocarriers synthesized from different amounts of parent silicalite and SiMCM-41. Then, the amount of mesophase and microphase may be determined from an X-Ray diffraction measurement.

In some embodiments, the pores of the porous silicate material are ordered. Such an ordering may form an ordered pore framework. The ordered structure of the framework may be a result of a template employed in the process of preparing the carrier particles. A specific template may assist in forming a specific pore structure. For example, a tetrapropylammonium hydroxide template may facilitate the formation of an MFI-type structure, while a quaternary ammonium cetyltrimethylammonium bromide, may assist in the formation of cylindrical pores which form a hexagonal structure. The ordered structure may allow for improved diffusion of materials into and out of the carrier particles. This characteristic may make the carrier particles useful as drug delivery agents.

In general, the particles of a porous silicate material can be any shape known to one of ordinary skill in the art. Examples of suitable shapes the particles may take include spheres, spheroids, lentoids, ovoids, solid polyhedra such as tetrahedra, cubes, octahedra, icosahedra, dodecahedra, rectangular prisms, hollow polyhedra (also known as nanocages), stellated polyhedral (both regular and irregular, also known as nanostars), triangular prisms (also known as nanotriangles), nanoplatelets, nanodisks, blocks, flakes, discs, granules, angular chunks, hollow spherical shells (also known as nanoshells), tubes (also known as nanotubes), rods (also known as nanorods), and mixtures thereof. In the case of nanorods, the rod shape may be defined by a ratio of a rod length to a rod width, the ratio being known as the aspect ratio. For particles of a porous silicate material of the current invention, nanorods should have an aspect ratio less than 1000, preferably less than 750, preferably less than 500, preferably less than 250, preferably less than 100, preferably less than 75, preferably less than 50, preferably less than 25. Nanorods having an aspect ratio greater than 1000 are typically referred to as nanowires and are not a shape that the particles of a porous silicate material are envisioned as having in any embodiments.

In some embodiments, the particles have uniform shape. Alternatively, the shape may be non-uniform. As used herein, the term "uniform shape" refers to an average consistent shape that differs by no more than 10%, by no more than 5%, by no more than 4%, by no more than 3%, by no more than 2%, by no more than 1% of the distribution of particles having a different shape. As used herein, the term "non-uniform shape" refers to an average consistent shape that differs by more than 10% of the distribution of particles having a different shape. In one embodiment, the shape is uniform and at least 90% of the particles are spherical or substantially circular, and less than 10% are polygonal. In another embodiment, the shape is non-uniform and less than 90% of the particles are spherical or substantially circular, and greater than 10% are polygonal.

In embodiments where the particles are spherical, the particle size may refer to a particle diameter. In embodiments where the particles are polyhedral, the particle size may refer to the diameter of a circumsphere. In some embodiments, the particle size refers to a mean distance from a particle surface to particle centroid or center of mass. In alternative embodiments, the particle size refers to a maximum distance from a particle surface to a particle centroid or center of mass. In some embodiments where the particles have an anisotropic shape such as nanorods, the particle size may refer to a length of the nanorod, a width of the nanorod, or an average of the length and width of the nanorod. In some embodiments, the particle size refers to the diameter of a sphere having an equivalent volume as the particle.

In some embodiments, the particles are monodisperse, having a coefficient of variation or relative standard deviation, expressed as a percentage and defined as the ratio of the particle size standard deviation (o) to the particle size mean (u) multiplied by 100 of less than 25%, preferably less than 10%, preferably less than 8%, preferably less than 6%, preferably less than 5%, preferably less than 4%, preferably less than 3%, preferably less than 2%. In some embodiments, the particles of the present disclosure are monodisperse having a particle size distribution ranging from 80% of the average particle size to 120% of the average particle size, preferably 90-110%, preferably 95-105% of the average particle size. In some embodiments, the particles are not monodisperse.

In general, the particle size may be determined by any suitable method known to one of ordinary skill in the art. In some embodiments, the particle size is determined by powder X-ray diffraction (PXRD). Using PXRD, the particle size may be determined using the Scherrer equation, which relates the full-width at half-maximum (FWHM) of diffraction peaks to the size of regions comprised of a single crystalline domain (known as crystallites) in the sample. In some embodiments, the crystallite size is the same as the particle size. For accurate particle size measurement by PXRD, the particles should be crystalline, comprise only a single crystal, and lack non-crystalline portions. Typically, the crystallite size underestimates particle size compared to other measures due to factors such as amorphous regions of particles, the inclusion of non-5 crystalline material on the surface of particles such as bulky surface ligands, and particles which may be composed of multiple crystalline domains. In some embodiments, the particle size is determined by dynamic light scattering (DLS). DLS is a technique which uses the time-dependent fluctuations in light scattered by particles in suspension or solution in a solvent, typically water to measure a size distribution of the particles. Due to the details of the DLS setup, the technique measures a hydrodynamic diameter of the particles, which is the diameter of a sphere with an equivalent diffusion coefficient as the particles. The hydrodynamic diameter may include factors not accounted for by other methods such as non-crystalline material on the surface of particles such as bulky surface ligands, amorphous regions of particles, and surface ligand-solvent interactions. Further, the hydrodynamic diameter may not accurately account for non-spherical particle shapes. DLS does have an advantage of being able to account for or more accurately model solution or suspension behavior of the particles compared to other techniques. In some embodiments, the particle size is determined by electron microscopy techniques such as scanning electron microscopy (SEM) or transmission electron microscopy (TEM).

In an embodiment, the carrier particles are particles of mesoporous silica which are substantially spherical and have a mean particle size of 50 to 110 nm, preferably 55 to 105 nm, preferably 60 to 100 nm, preferably 65 to 95 nm preferably 70 to 90 nm, preferably 75 to 85 nm, preferably 80 nm. In an embodiment, the carrier particles are particles of mesoporous silica which are amorphous by Powder X-ray Diffraction (PXRD).

In some embodiments, the particles are particles of porous silicate material selected from a group including silicalite, mesosilicalite, silver-incorporated silicalite, and silver-incorporated mesosilicalite having a mean particle size of 25 to 400 nm, preferably 30 to 375 nm, preferably 40 to 350 nm, preferably 50 to 325 nm, preferably 60 to 300 nm, preferably 75 to 275 nm, preferably 100 to 250 nm.

In some embodiments, the carrier particles are particles of silver-incorporated mesosilicalite having a silicon to silver mole ratio of 10:1 to 150:1, preferably 12.5:1 to 125:1, preferably 15:1 to 120:1, preferably 17.5:1 to 115:1, preferably 20:1 to 110:1, preferably 22.5:1 to 105:1, preferably 25:1 to 100:1. In some embodiments, the carrier particles are particles of silver-incorporated silicalite having a silicon to silver mole ratio of 10:1 to 150:1, preferably 12.5:1 to 125:1, preferably 15:1 to 120:1, preferably 17.5:1 to 115:1, preferably 20:1 to 110:1, preferably 22.5:1 to 105:1, preferably 25:1 to 100:1. In silver incorporated silicalite and silver-incorporated mesosilicalite, silver atoms are incorporated into the structure of the silicate material. For example, the silver atoms may be isomorphously substituted into the framework of the silicalite or mesosilicalite. Such incorporation is distinct from physisorption or chemisorption or other similar interaction within the pores of the silicate material. The silver atoms may be present in any suitable oxidation state, such as 0, +1, or +2. The silver atoms may be present as isolated silver atoms or ions. Such isolated silver atoms ions may be coordinated to oxygen atoms and/or silicon atoms present in the silicate material. In some embodiments, the silver atoms ions are present as substitutional dopants. Such substitutional dopants may take the place of silicon atoms in the silicate material. In some embodiments, the silver atoms ions are present as interstitial dopants. Such interstitial dopants may be present in voids or other similar spaces between atoms or polyatomic ions such as silicate tetrahedral present in the silicate material. In some embodiments, the silver atoms ions are present as clusters containing 2 to 25 silver atoms or ions.

The medicinal nanocomposite further includes 0.5 to 10 wt. %, preferably 0.75 to 8 wt. %, preferably 1 to 6 wt. % silver nanoparticles (Ag NPs) dispersed on the pore framework. The silver nanoparticles may be disposed on an interior pore surface of the carrier particles and/or an exterior surface of the carrier particles. In some embodiments, the silver nanoparticles have a mean particle size of 5 to 50 nm, preferably 10 to 40 nm, preferably 15 to 35 nm, preferably 20 to 30 nm, preferably 25 nm. In some embodiments, the silver nanoparticles are crystalline by PXRD. The silver nanoparticles are distinct from the silver atoms present in silver-doped silicalite and/or silver-doped mesosilicalite. The silver nanoparticles may be any suitable shape as described above. In some embodiments, the silver nanoparticles are spherical.

The medicinal nanocomposite further includes 0.5 to 10 wt. %, preferably 2 to 8 wt. %, preferably 1.5 to 9 wt. %, preferably 2.5 to 7.5 wt. %, preferably 3 to 7 wt. %, preferably 3.5 to 6.5 wt. %, preferably 4 to 6 wt. %, preferably 4.5 to 5.5 wt. %, preferably 5 wt. % of a platinum-containing pharmaceutical compound disposed on at least one surface selected from the interior pore surface of the carrier particles, the exterior surface of the carrier particles, and a surface of the silver nanoparticles. In some embodiments, the platinum-containing pharmaceutical compound is at least one selected from a group including cisplatin, oxaliplatin, and carboplatin. In some embodiments, the platinum-containing pharmaceutical compound is cisplatin.

The medicinal nanocomposite releases less than 10 mole %, preferably less than 9.75 mole %, preferably less than 9.5 mole %, preferably less than 9.25 mole %, preferably less than 9.0 mole %, preferably less than 8.75 mole %, preferably less than 8.5 mole %, preferably less than 8.25 mole %, preferably less than 8.0 mole %, preferably less than 7.9 mole %, of the platinum-containing pharmaceutical compound after 60 to 84 hours, preferably 62 to 82 hours, preferably 64 to 80 hours, preferably 66 to 78 hours, preferably 68 to 76 hours, preferably 69 to 75 hours, preferably 70 to 74 hours, preferably 71 to 73 hours, preferably 72 hours at a pH of 4.5 to 7, based on an initial amount of the platinum-containing pharmaceutical compound present in the medicinal nanocomposite. In some embodiments, the release takes place upon contact with a suitable biological medium. Examples of suitable biological media include, but are not limited to, buffered saline solutions such as phosphate buffered saline, cell culture media such as Minimum Essential Medium (MEM, also known as Eagle's minimal essential medium EMEM), Dulbecco's Modified Eagle's Medium (DMEM), Iscove's Modified Dulbecco's Medium (IMDM), RPMI-1640, Ham's F-10, and F-12; animal tissue, or a subject's body.

In some embodiments, the medicinal nanocomposite has a mean pore size of 15 to 27.5 nm, preferably 15.5 to 27 nm, preferably 16 to 26 nm, preferably 17 to 25 nm, preferably 18 to 24 nm, preferably 19 to 23 nm, preferably 19.5 to 22 nm, preferably 20 to 21 nm. In some embodiments, the medicinal nanocomposite has a mean pore volume of 0.05 to 0.35 $cm^3/g$, preferably 0.06 to 0.033 $cm^3/g$, preferably 0.07 to 0.3 $cm^3/g$, preferably 0.08 to 0.28 $cm^3/g$. In some embodiments, the medicinal nanocomposite has a mean surface are of 7.5 to 75 $m^2/g$, preferably 10 to 70 $m^2/g$, preferably 12.5 to 65 $m^2/g$, preferably 15 to 60 $m^2/g$, preferably 17 to 56 $m^2/g$.

In an aspect, the present disclosure provides a coated nanocomposite. The coated nanocomposite includes 80 to 99 wt. % of the medicinal nanocomposite and 1 to 20 wt. % of a biocompatible coating. In general, the biocompatible coating may be any suitable coating known to one of ordinary skill in the art. Examples of such suitable biocompatible coatings include, but are not limited to, agarose, agar, carrageen, alginic acid, alginate, an alginic acid derivative, a hyaluronate derivative, a polyanionic polysaccharide, chitin, chitosan, fibrin, a polyglycolide, a polylactide, a polycaprolactone, a dextran or copolymer thereof, polyvinyl pyrrolidone, a polyacrylate, a wax, a polyethylene-polyoxypropylene-block polymer, wool fat, poly(L-lactic acid), poly (DL-Lactic acid) copoly(lactic/glycolic acid), cellulose, a cellulose derivative, a glycol, polylactide-polyglycolide, polymethyldisiloxane, polycaprolactone, polylactic acid, and ethylene vinyl acetate. In some embodiments, the biocompatible coating comprises at least one selected from a group including polyethylene glycol, polypropylene glycol, polylactic acid, polyvinyl alcohol, polyvinyl pyrrolidone, alginate, chitosan, dextran, and hyaluronic acid.

One aspect that may be positively affected by the simultaneous presence of the silver nanoparticles and the platinum-containing pharmaceutical compound is the release rate of the platinum-containing pharmaceutical compound. The silver nanoparticles may inhibit release of the platinum-containing pharmaceutical compound for a time period while the medicinal nanocomposite travels through the vascular system of a patient undergoing treatment. This provides an induction period during which only minor amounts of the platinum-containing pharmaceutical compound are released. In some embodiments, the induction period is provided by a coating disposed on the medicinal nanocomposite, the coating as described above. In such embodiments, the coating may inhibit the release of the pharmaceutical agent mixture. Removal of the coating by any suitable process, for example by dissolving, degrading, or digesting, may allow the pharmaceutical gent mixture to be released.

Referring to FIG. 1, a schematic flow diagram of a method 100 of forming the medicinal nanocomposite is illustrated. The method 100 is described with reference to formation of the porous silicate material illustrated in FIG. 2. The order in which the method 100 is described is not intended to be construed as a limitation, and any number of the described method steps can be combined in any order to implement the method 100. Additionally, individual steps may be removed or skipped from the method 100 without departing from the spirit and scope of the present disclosure.

At step 102, the method 100 includes aging a reaction mixture including a silver source and particles of the porous silicate material in a first solvent for 4 to 24, preferably 6 to 20 hours, preferably 8 to 16 hours, preferably 10 to 14 hours, preferably 11 to 13 hours, preferably 12 hours to form an aged mixture. The silver source may be any suitable silver source known to one of ordinary skill in the art. Examples of suitable silver sources include silver halides such as silver chloride, silver bromide, and silver iodide, silver nitrate, silver acetate, silver sulfate, silver bromate, silver iodate, silver nitrite, silver carbonate. In some embodiments, the silver source is a silver halide or a silver nitrate. In an embodiment, the silver source is silver nitrate. In some embodiments, the porous silicate material is selected from a group including silver-incorporated silicalite and silver-incorporated mesosilicalite. In some embodiments, the porous silicate material is selected from a group including silicalite and mesosilicalite. In some embodiments, the porous silicate material is mesoporous silica. In some embodiments, the first solvent is water.

At step 104, the method 100 includes heating the aged mixture to 90 to 150° C. for 2 to 12 hours, preferably 3 to 10 hours, preferably 4 to 8 hours, preferably 5 to 7 hours, preferably 6 hours to form a first product.

At step 106, the method 100 includes calcining the first product at 350 to 650° C., preferably 375 to 625° C., preferably 400 to 600° C., preferably 425 to 575° C., preferably 450 to 550° C., preferably 475 to 525° C., preferably 500° C. for 1 to 6 hours to form a second product.

At step 108, the method 100 includes mixing the second product and the platinum-containing pharmaceutical compound in a second solvent for 2 to 12 hours, preferably 4 to 1-hours, preferably 6 to 8 hours at −15 to 15° C., preferably −12.5 to 12.5 C, preferably −10 to 10° C., preferably −7.5 to 7.5° C., preferably −5 to 5° C., preferably −2.5 to 2.5° C., preferably 0° C. to form the medicinal nanocomposite. The platinum-containing pharmaceutical compound is one or cisplatin, oxaliplatin, and carboplatin. In some embodiments, the pharmaceutical compound is cisplatin. In some embodiments, the second solvent is a normal saline solution.

At step 110, the method 100 includes isolating the medicinal nanocomposite. In general, the medicinal nanocomposite may be isolated by any suitable technique for separating a solid and liquid. Examples of such suitable techniques include, but are not limited to decantation, centrifugation, evaporation, and filtration, but excluding techniques such as distillation. In an embodiment, the medicinal nanocomposite may be isolated by filtration. In some embodiments, the medicinal nanocomposite may be isolated by evaporating a remaining second solvent.

In some embodiments, the method further comprises reducing to smaller particles at least one material selected from the group consisting of the medicinal nanocomposite, the second product, and the first product. Such a reduction to smaller particles may be performed by any suitable technique or with any suitable equipment known to one of ordinary skill in the art. Examples of such techniques include, but are not limited to, milling, grinding, ball milling, chopping, pulverizing, crushing, pounding, mincing, shredding, smashing, and fragmenting. In some embodiments, the milling may take place using a mill, ball mill, rod mill, autogenous mill, cutting mill, semi-autogenous grinding mill, pebble mill, buhrstone mill, burr mill, tower mill, vertical shaft impactor mill, a low energy milling machine, grinder, pulverizer, mortar and pestle, blender, crusher, or other implement used to reduce a material to small particles. Such reduction to smaller particles may be useful for disrupting aggregates or agglomerates which may have formed during the steps of the method. Such reduction may be performed at any suitable point in the method.

Figure 2:
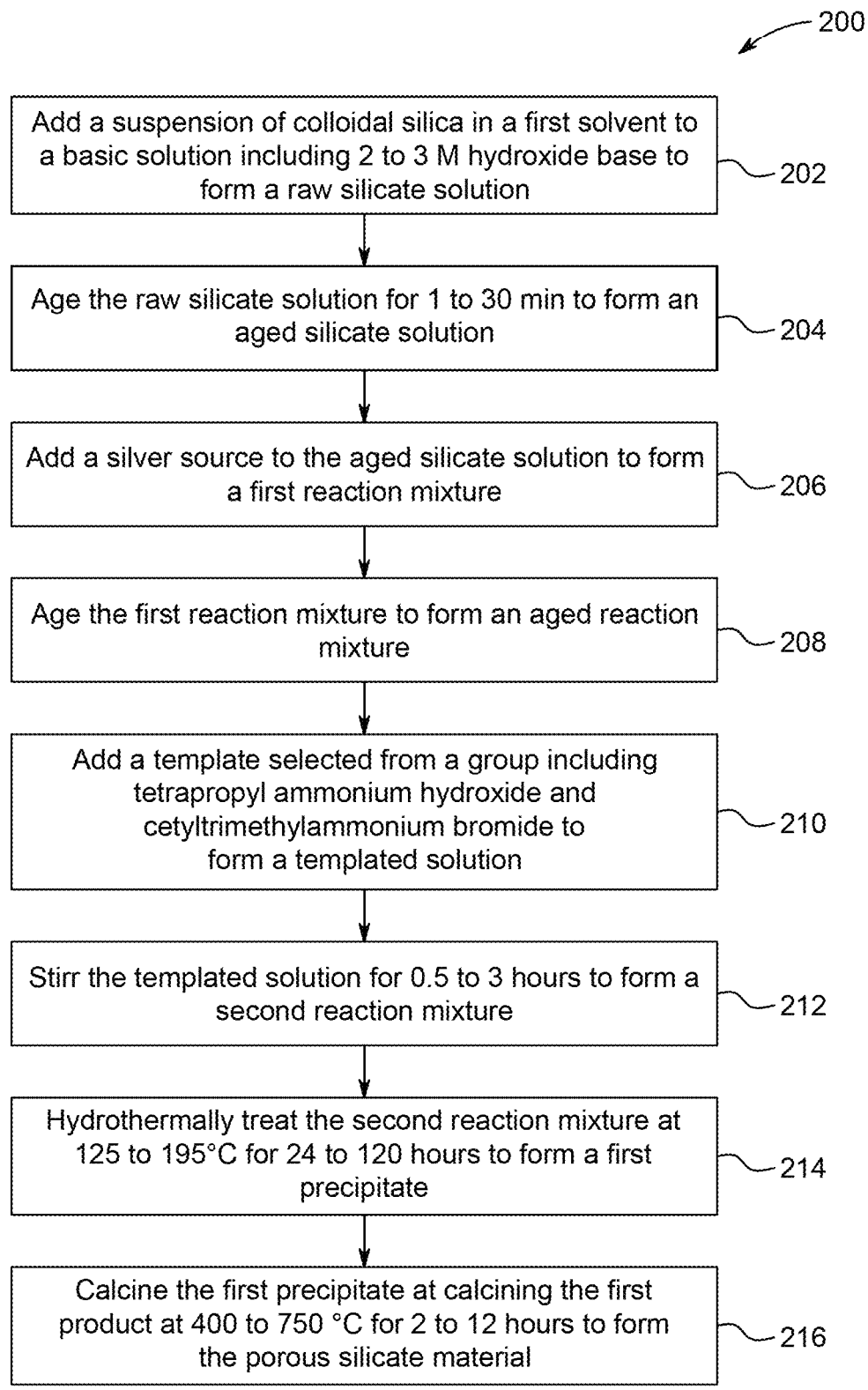
FIG. 2 is a schematic flow diagram of a method of making a porous silicate material, according to certain embodiments.

Referring to FIG. 2, a schematic flow diagram of a method 200 of making the porous silicate material is illustrated. The order in which the method 200 is described is not intended to be construed as a limitation, and any number of the described method steps can be combined in any order to implement the method 200. Additionally, individual steps may be removed or skipped from the method 200 without departing from the spirit and scope of the present disclosure.

At step 202, method 200 includes adding a suspension of colloidal silica in the first solvent to a basic solution including 2 to 3 M, preferably 2.1 to 2.9 M, preferably 2.25 to 2.75 M, preferably 2.3 to 2.7 M, preferably 2.4 to 2.6 M hydroxide base to form a raw silicate solution. In an embodiment, the colloidal silica is Ludox® AS-40. In an embodiment, the hydroxide base is at least one selected from the group consisting of sodium hydroxide, potassium hydroxide, and ammonium hydroxide. In some embodiments, the hydroxide base is sodium hydroxide.

At step 204, method 200 includes aging the raw silicate solution for 1 to 30 minutes, preferably 2.5 to 27.5 minutes, preferably 5 to 25 minutes, preferably 7.5 to 22.5 minutes, preferably 10 to 20 minutes, preferably 12.5 to 17.5 minutes, preferably 15 minutes to form an aged silicate solution.

At step 206, method 200 includes adding a silver source to the aged silicate solution to form a first reaction mixture. The silver source may be as described above.

At step 208, method 200 includes aging the first reaction mixture to form an aged reaction mixture. In some embodiments, the first reaction mixture is aged for 1 to 30 minutes, preferably 2.5 to 27.5 minutes, preferably 5 to 25 minutes, preferably 7.5 to 22.5 minutes, preferably 10 to 20 minutes, preferably 12.5 to 17.5 minutes, preferably 15 minutes.

At step 210, method 200 includes adding a template selected from a group including tetrapropyl ammonium hydroxide and cetyltrimethyl ammonium bromide to form a templated solution. In some embodiments, the template is tetrapropyl ammonium hydroxide. In some embodiments, the template is tetrapropyl ammonium hydroxide and the porous silicate material is silicalite or silver-incorporated silicalite. In some embodiments, the template: is cetyltrimethylammonium bromide. In some embodiments, the template is cetyltrimethylammonium bromide and the porous silicate material is mesosilicalite or silver-incorporated mesosilicalite.

At step 212, method 200 includes stirring the templated solution for 0.5 to 3 hours, preferably 0.75 to 2.5 hours, preferably 1 to 2 hours, preferably 1.25 to 1.75 hours, preferably 1.5 hours to form a second reaction mixture.

At step 214, method 200 includes hydrothermally treating the second reaction mixture at 125 to 195° C., preferably 130 to 190° C., preferably 135 to 185° C., preferably 140 to 180° C., preferably 145 to 175° C., preferably 150 to 170° C., preferably 155 to 165° C., preferably 160° C. for 24 to 120 hours, preferably 30 to 114 hours, preferably 36 to 108 hours, preferably 42 to 102 hours, preferably 48 to 96 hours, preferably 54 to 90 hours, preferably 60 to 84 hours, preferably 63 to 81 hours, preferably 66 to 78 hours, preferably 68 to 76 hours, preferably 70 to 74 hours, preferably 72 hours to form a first precipitate. The first precipitate may be isolated as described above. In some embodiments, the first precipitate may be isolated by filtration. In some embodiments, the first precipitate may be washed with a solvent. In some embodiments, the solvent may be an alcohol or water or a combination of both. The alcohol may be ethanol, isopropyl alcohol, or any lower alcohol (i.e. an alcohol having 5 or fewer carbon atoms, preferably 4 or fewer carbon atoms, preferably 3 or fewer carbon atoms). In some embodiments, the solvent is a solution of ethanol and water.

At step 216, method 200 includes calcining the first precipitate at 400 to 750° C., preferably 425 to 725° C., preferably 450 to 700° C., preferably 475 to 675° C., preferably 500 to 600° C., preferably 525 to 575° C., preferably 550° C. for 2 to 12 hours, preferably 4 to 10 hours, preferably 5 to 8 hours, preferably 6 hours to form the porous silicate material. In some embodiments, the porous silicate material is selected from a group including mesoporous silica, silicalite, mesosilicalite, silver-incorporated silicalite, and silver-incorporated mesosilicalite. In some embodiments, the porous silicate material may include, but not limited to, monodispersed spherical silica (MSS), Santa Barbara Amorphous-16 (SBA-16), TiZSM-5 (Zeolite Socony Mobil #5), mesosilicalite, halloysite, and Ag-silicalite. In an embodiment, the porous silicate material is TiZSM.

In an aspect, the present disclosure provides a method of treating cervical cancer, colorectal cancer, or both in a subject. In some embodiments, the subject may be an animal. In some embodiments, the subject is a mammal. In some embodiments, the subject is a human. The method includes administering to the subject an effective amount of the medicinal nanocomposite. As used herein, "effective amount" refers to a dose or concentration of a drug that produces a biological response. In some embodiments, the medicinal nanocomposite is administered as a pharmaceutical composition comprising the medicinal nanocomposite. The pharmaceutical composition may further comprise one or more pharmaceutically acceptable carriers.

As used herein, a "pharmaceutically acceptable carrier" refers to a carrier or diluent that does not cause significant irritation to an organism, does not abrogate the biological activity and properties of the administered active ingredient, and/or does not interact in a deleterious manner with the other components of the composition in which it contains. The term "carrier" encompasses any excipient, binder, diluent, filler, salt, buffer, solubilizer, lipid, stabilizer, or other material well-known in the art for use in pharmaceutical formulations. The choice of a carrier for use in a pharmaceutical composition will depend upon the intended route of administration for the pharmaceutical composition. The preparation of pharmaceutically acceptable carriers and formulations containing these materials is described in, e.g. Remington's Pharmaceutical Sciences, 21st Edition, ed. University of the Sciences in Philadelphia, Lippincott, Williams & Wilkins, Philadelphia Pa., 2005, which is incorporated herein by reference in its entirety). Examples of physiologically acceptable carriers include antioxidants including ascorbic acid; low molecular weight (less than about 10 residues) peptides; proteins, such as serum albumin, gelatine, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrin; chelating agents such as EDTA; sugar alcohols such as mannitol or sorbitol; salt-forming counter ions such as sodium; and/or non-ionic surfactants such as TWEEN® (ICI, Inc.; Bridgewater, N.J.), polyethylene glycol (PEG), and PLURONICS™ (BASF; Florham Park, N.J.). An "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatine, vegetable oils, and polyethylene glycols.

In some embodiments, the pharmaceutically acceptable carrier and/or excipient is at least one selected from the group consisting of a buffer, an inorganic salt, a fatty acid, a vegetable oil, a synthetic fatty ester, a surfactant, and a polymer.

Exemplary buffers include, without limitation, phosphate buffers, citrate buffer, acetate buffers, borate buffers, carbonate buffers, bicarbonate buffers, and buffers with other organic acids and salts.

Exemplary inorganic salts include, without limitation, calcium carbonate, calcium phosphate, disodium hydrogen phosphate, potassium hydrogen phosphate, sodium chloride, zinc oxide, zinc sulfate, and magnesium trisilicate.

Exemplary fatty acids include, without limitation, an omega-3 fatty acid (e.g., linolenic acid, docosahexaenoic acid, eicosapentaenoic acid) and an omega-6 fatty acid (e.g., linoleic acid, eicosadienoic acid, arachidonic acid). Other fatty acids, such as oleic acid, palmitoleic acid, palmitic acid, stearic acid, and myristic acid, may be included.

Exemplary vegetable oils include, without limitation, avocado oil, olive oil, palm oil, coconut oil, rapeseed oil, soybean oil, corn oil, sunflower oil, cottonseed oil, and peanut oil, grape seed oil, hazelnut oil, linseed oil, rice bran oil, safflower oil, sesame oil, brazil nut oil, carapa oil, passion fruit oil, and cocoa butter.

Exemplary synthetic fatty esters include, without limitation, methyl, ethyl, isopropyl and butyl esters of fatty acids (e.g., isopropyl palmitate, glyceryl stearate, ethyl oleate, isopropyl myristate, isopropyl isostearate, diisopropyl sebacate, ethyl stearate, di-n-butyl adipate, dipropylene glycol pelargonate), C12-C16 fatty alcohol lactates (e.g., cetyl lactate and lauryl lactate), propylene dipelargonate, 2-ethylhexyl isononoate, 2-ethylhexyl stearate, isopropyl lanolate, 2-ethylhexyl salicylate, cetyl myristate, oleyl myristate, oleyl stearate, oleyl oleate, hexyl laurate, isohexyl laurate, propylene glycol fatty ester, and polyoxyethylene sorbitan fatty ester. As used herein, the term "propylene glycol fatty ester" refers to a monoether or diester, or mixtures thereof, formed between propylene glycol or polypropylene glycol and a fatty acid. The term "polyoxyethylene sorbitan fatty ester" denotes oleate esters of sorbitol and its anhydrides, typically copolymerized with ethylene oxide.

Surfactants may act as detergents, wetting agents, emulsifiers, foaming agents, and dispersants. Surfactants that may be present in the compositions of the present disclosure include zwitterionic (amphoteric) surfactants, e.g., phosphatidylcholine, and 3-[(3-cholamidopropyl)dimethylammonio]-1-propanesulfonate (CHAPS), anionic surfactants, e.g., sodium lauryl sulfate, sodium octane sulfonate, sodium decane sulfonate, and sodium dodecane sulfonate, non-ionic surfactants, e.g., sorbitan monolaurate, sorbitan monopalmitate, sorbitan trioleate, polysorbates such as polysorbate 20 (Tween 20), polysorbate 60 (Tween 60), and polysorbate 80 (Tween 80), cationic surfactants, e.g., decyltrimethylammonium bromide, dodecyltrimethyl-ammonium bromide, tetradecyltrimethylammonium bromide, tetradecyltrimethylammonium chloride, and dodecylammonium chloride, and combinations thereof.

Exemplary polymers include, without limitation, polylactides, polyglycolides, polycaprolactones, polyanhydrides, polyurethanes, polyesteramides, polyorthoesters, polydioxanones, polyacetals, polyketals, polycarbonates, polyorthocarbonates, polyphos-phazenes, polyhydroxybutyrates, polyhydroxyvalerates, polyalkylene oxalates, polyalkylene succinates, poly(malic acid), poly(maleic anhydride), a polyvinyl alcohols, and copolymers, terpolymers, or combinations or mixtures therein. The copolymer/terpolymer may be a random copolymer/terpolymer, or a block copolymer/terpolymer.

Depending on the route of administration e.g. oral, parental, or topical, the pharmaceutical composition may be in the form of solid dosage form such as tablets, caplets, capsules, powders, and granules, semi-solid dosage form such as gels, pastes, and suppositories, liquid dosage forms such as suspension, and dispersions, inhalation dosage form such as aerosols, sprays, and powders.

Solid dosage forms for oral administration can include capsules, tablets, pills, powders, and granules. In such solid dosage forms, the active ingredient is ordinarily combined with one or more adjuvants appropriate to the indicated route of administration. If administered per os, the active ingredient can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatine, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering ingredients such as sodium citrate, magnesium or calcium carbonate or bicarbonate. Tablets and pills can additionally be prepared with enteric coatings.

Liquid dosage forms for oral administration can include pharmaceutically acceptable emulsions, suspensions, syrups, and elixirs containing inert diluents commonly used in the art, such as water. Such pharmaceutical compositions can also comprise adjuvants, such as wetting ingredients, emulsifying and suspending ingredients, and sweetening, flavoring, and perfuming ingredients.

For therapeutic purposes, formulations for parenteral administration can be in the form of aqueous or non-aqueous isotonic sterile injection dispersions or suspensions. The term "parenteral", as used herein, includes intravenous, intravesical, intraperitoneal, subcutaneous, intramuscular, intralesional, intracranial, intrapulmonal, intracardial, intrasternal, and sublingual injections, or infusion techniques. These dispersions and suspensions can be prepared from sterile powders or granules having one or more of the carriers or diluents mentioned for use in the formulations for oral administration. The active ingredient can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Injectable preparations, for example, sterile injectable aqueous or oleaginous suspensions can be formulated according to the known art using suitable dispersing or wetting ingredients and suspending ingredients. The sterile injectable preparation can also be a sterile injectable dispersion or suspension in a non-toxic parenterally acceptable diluent or solvent, for example, in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids, such as oleic acid, find use in the preparation of injectable. Dimethylacetamide, surfactants including ionic and non-ionic detergents, polyethylene glycols can be used. Mixtures of solvents and wetting ingredients such as those discussed above are also useful.

Suppositories for rectal administration can be prepared by mixing the active ingredient with a suitable non-irritating excipient, such as cocoa butter, synthetic mono-, di-, or triglycerides, fatty acids, and polyethylene glycols that are solid at ordinary temperatures but liquid at the rectal temperature and will therefore melt in the rectum and release the drug. Such suppositories may be advantageous for treating colorectal cancer, but may be unsuitable for treating other cancers.

Intravaginal administration may be advantageous for treating cervical cancer, but may be unsuitable for treating other cancers.

Administration by inhalation may be advantageous for treating lung cancer, but may be unsuitable for treating other cancers.

In other embodiments, the pharmaceutical composition comprising the medicinal nanocomposite disclosed herein thereof has different release rates categorized as immediate release and controlled- or sustained-release.

As used herein, the terms "treat", "treatment", and "treating" in the context of the administration of a therapy to a subject in need thereof refers to the reduction or inhibition of the progression and/or duration of a disease (e.g. cancer), the reduction or amelioration of the severity of the disease, and/or the amelioration of one or more symptoms thereof resulting from the administration of one or more therapies. "Treating" or "treatment" of the disease includes preventing the disease from occurring in a subject that may be predisposed to the disease but does not yet experience or exhibit symptoms of the disease (prophylactic treatment), inhibiting the disease (slowing or arresting its development), ameliorating the disease, providing relief from the symptoms or side-effects of the disease (including palliative treatment), and relieving the disease (causing regression of the disease). With regard to the disease, these terms simply mean that one or more of the symptoms of the disease will be reduced. Such terms may refer to one, two, three, or more results following the administration of one, two, three, or more therapies: (1) a stabilization, reduction (e.g. by more than 10%, 20%, 30%, 40%, 50%, preferably by more than 60% of the population of cancer cells and/or tumour size before administration), or elimination of the cancer cells, (2) inhibiting cancerous cell division and/or cancerous cell proliferation, (3) relieving to some extent (or, preferably, eliminating) one or more symptoms associated with a pathology related to or caused in part by unregulated or aberrant cellular division, (4) an increase in disease-free, relapse-free, progression-free, and/or overall survival, duration, or rate, (5) a decrease in hospitalization rate, (6) a decrease in hospitalization length, (7) eradication, removal, or control of primary, regional and/or metastatic cancer, (8) a stabilization or reduction (e.g. by at least 10%, 20%, 30%, 40%, 50%, 60%, 70%, preferably at least 80% relative to the initial growth rate) in the growth of a tumor or neoplasm, (9) an impairment in the formation of a tumor, (10) a reduction in mortality, (11) an increase in the response rate, the durability of response, or number of patients who respond or are in remission, (12) the size of the tumor is maintained and does not increase or increases by less than 10%, preferably less than 5%, preferably less than 4%, preferably less than 2%, (13) a decrease in the need for surgery (e.g. colectomy, mastectomy), and (14) preventing or reducing (e.g. by more than 10%, more than 30%, preferably by more than 60% of the population of metastasized cancer cells before administration) the metastasis of cancer cells.

The term "subject" and "patient" are used interchangeably. As used herein, they refer to any subject for whom or which therapy, including with the pharmaceutical compositions according to the present disclosure is desired. In most embodiments, the subject is a mammal, including but is not limited to a human, a non-human primate such as a chimpanzee, a domestic livestock such as a cattle, a horse, a swine, a pet animal such as a dog, a cat, and a rabbit, and a laboratory subject such as a rodent, e.g. a rat, a mouse, and a guinea pig. In preferred embodiments, the subject is a human.

As used herein, a subject in need of therapy includes a subject already with the disease, a subject which does not yet experience or exhibit symptoms of the disease, and a subject predisposed to the disease. In preferred embodiments, the subject is a person who is predisposed to cancer, e.g. a person with a family history of cancer. People who (i) had inflammatory bowel disease, or a genetic syndrome such as familial adenomatous polyposis (FAP) and hereditary non-polyposis colorectal cancer (Lynch syndrome), and/or (ii) consumes a low-fiber and high-fat diet are at a higher risk of contracting colon cancer. People with a cervix who have been infected with the human papilloma virus (HPV) are at a higher risk of contracting cervical cancer. White women or a person with (i) certain inherited genes (e.g. mutated BRCA1, BRCA2, ATM, TP53, CHEK2, PTEN, CDH1, STK11, and PALB2), (ii) radiation occurred to one's chest, and/or (iii) exposure to diethylstilbestrol (DES) are at a higher risk of contracting breast cancer. People who (i) smoke or regularly breathe in second-hand smoke, (ii) exposed to carcinogens including, but not limited to polycyclic aromatic hydrocarbons (e.g. benzo[a]pyrene, benz[a]anthracene, and methylated derivatives thereof), asbestos, radioactive substances (e.g., uranium, radon), and/or (iii) inhaled chemicals or minerals (e.g., arsenic, beryllium, cadmium, silica, vinyl chloride, nickel compounds, chromium compounds, coal products, mustard gas, and chloromethyl ethers) are at a higher risk of contracting lung cancer.

The terms "administer", "administering", "administration", and the like, as used herein, refer to the methods that may be used to enable delivery of the active ingredient and/or the composition to the desired site of biological action. Routes or modes of administration are as set forth herein. These methods include, but are not limited to, oral routes, intraduodenal routes, parenteral injection (including intravenous, subcutaneous, intraperitoneal, intramuscular, intravascular, or infusion), and rectal administration. Those of ordinary skill in the art are familiar with administration techniques that can be employed with the compounds and methods described herein. In preferred embodiments, the active ingredient and/or the pharmaceutical composition described herein are administered orally.

The dosage amount and treatment duration are dependent on factors, such as bioavailability of a drug, administration mode, toxicity of a drug, gender, age, lifestyle, body weight, the use of other drugs and dietary supplements, the disease stage, tolerance and resistance of the body to the administered drug, etc., and then determined and adjusted accordingly. The terms "effective amount", "therapeutically effective amount", "pharmaceutically effective amount" or "sufficient amount" refer to that amount of the active ingredient being administered which will relieve to some extent one or more of the symptoms of the disease being treated. The result can be a reduction and/or alleviation of the signs, symptoms, or causes of a disease, or any other desired alteration of a biological system. An appropriate "effective amount" may differ from one individual to another. An appropriate "effective amount" in any individual case may be determined using techniques, such as a dose escalation study. In some embodiments, an effective amount is in the range of 0.1-30 g/kg of the medicinal nanocomposite per body weight of the subject.

In treating certain cancers, the best approach is often a combination of surgery, radiotherapy, and/or chemotherapy. Therefore, in at least one embodiment, the pharmaceutical composition is employed in conjunction with radiotherapy. In another embodiment, the pharmaceutical composition is employed with surgery. The radiotherapy and/or surgery may be before or after the composition is administered.

A treatment method may comprise administering the pharmaceutical composition of the current disclosure as a single dose or multiple individual divided doses and applying a magnetic field to the diseased tissue, wherein the medicinal nanocomposite is accumulated and releases the loaded anti-cancer therapeutic and/or antioxidant in or nearby the diseased tissues. In some embodiments, the pharmaceutical composition is administered at various dosages (e.g. a first dose with an effective amount of medicinal nanocomposite comprising 200 mg of the anti-cancer therapeutic per kilogram of the subject and a second dose with an effective amount of the medicinal nanocomposite comprising 50 mg of the anti-cancer therapeutic per kilogram of the subject). In some embodiments, the interval of time between the administration of the pharmaceutical composition and the administration of one or more additional therapies may be about 1-5 minutes, 1-30 minutes, 30 minutes to 60 minutes, 1 hour, 1-2 hours, 2-6 hours, 2-12 hours, 12-24 hours, 1-2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11-15 weeks, 15-20 weeks, 20-30 weeks, 30-40 weeks, 40-50 weeks, 1 month, 2 months, 3 months, 4 months, 5 months, 6 months, 7 months, 8 months, 9 months, 10 months, 11 months, 12 months, 1 year, 2 years, or any period of time in between. Preferably, the pharmaceutical composition is administered once daily for at least 2 days, 5 days, 6 days, or 7 days. In certain embodiments, the pharmaceutical composition and one or more additional therapies are administered less than 1 day, 1 week, 2 weeks, 3 weeks, 4 weeks, 1 month, 2 months, 3 months, 6 months, 1 year, 2 years, or 5 years apart.

The methods for treating cancer and other proliferative disorders described herein inhibit, remove, eradicate, reduce, regress, diminish, arrest or stabilize a cancerous tumor, including at least one of the tumor growth, tumor cell viability, tumor cell division and proliferation, tumor metabolism, blood flow to the tumor and metastasis of the tumor. In some embodiments, the size of a tumor, whether by volume, weight or diameter, is reduced after the treatment by at least 5%, 10%, 15%, 20%, 25%, 30%, 40%, 50%, 60%, 70%, 75%, 80%, 85%, 90%, 95%, 99%, or 100%, relative to the tumor size before treatment. In other embodiments, the size of a tumor after treatment does not reduce but is maintained the same as the tumor size before treatment. Methods of assessing tumor size include, but are not limited to, CT scan, MRI, DCE-MRI and PET scan.

In most embodiments of treatment, the method further comprises measuring a concentration of a biomarker and/or detecting a mutation in a biomarker before and/or after the pharmaceutical composition comprising the medicinal nanocomposite of the present disclosure is administered. As used herein, the term "biomarker" refers to a characteristic that is objectively measured and evaluated as an indicator of normal biological processes, pathogenic processes or pharmacological responses to a therapeutic intervention. Generic cancer biomarkers include circulating tumor DNA (ctDNA) and circulating tumor cells (CTC). Potentially predictive cancer biomarkers include, without limitation, mutations in genes BRCA1 and BRCA2 for breast cancer and/or ovarian cancer, overexpression of CEA, NSE, CYFRA-21-1, CA-125, and CA-199 for lung cancer, overexpression of TYMS, mutations in genes p53 and KRAS for colon cancer, and mutations in genes MED1, ERBB3, CASP8, HLA-A, and TGFBR2 for cervical cancer.

The mutation in the biomarker may be detected by any suitable procedure known to one of ordinary skill in the art, such as restriction fragment length polymorphism (RFLP), polymerase chain reaction (PCR) assay, multiplex ligation-dependent probe amplification (MLPA), denaturing gradient gel electrophoresis (DGGE), single-strand conformation polymorphism (SSCP), hetero-duplex analysis, protein truncation test (PTT), and oligonucleotide ligation assay (OLA). The procedures to detect the mutation are well-known to those of ordinary skill in the art.

The term "sample" used herein refers to any biological sample obtained from the subject in need of therapy including a single cell, multiple cells, fragments of cells, a tissue sample, and/or body fluid. Specifically, the biological sample may include red blood cells, white blood cells, platelets, hepatocytes, epithelial cells, endothelial cells, a skin biopsy, a mucosa biopsy, an aliquot of urine, saliva, whole blood, serum, plasma, lymph. In some embodiments, the biological sample is taken from a tumor.

The concentration level of the cancer biomarker in a sample may be measured by an assay, for example an immunoassay. Typical immunoassay methods include, without limitation, enzyme-linked immunosorbent assay (ELISA), enzyme-linked immunospot assay (ELISPOT), Western blotting, immunohistochemistry (IHC), immunocytochemistry, immunostaining, and multiple reaction monitoring (MRM) based mass spectrometric immunoassay. The protocol for measuring the concentration of the biomarker and/or detecting the mutation in the biomarker is known to those of ordinary skill, for example by performing the steps outlined in the commercially available assay kit sold by Sigma-Aldrich, Thermo Fisher Scientific, R & D Systems, ZeptoMetrix Inc., Cayman Inc., Abcam, Trevigen, Dojindo Molecular Technologies, Biovision, and Enzo Life Sciences.

In some embodiments, the concentration of the biomarker is measured before and after the administration. When the concentration of the biomarker is maintained, the method may further comprise increasing the effective amount of the medicinal nanocomposite by at least 5%, at least 10%, or at least 30%, up to 50%, up to 60%, or up to 80% of an initial effective amount medicinal nanocomposite that contains in the range of 1-300 mg of the anti-cancer therapeutic per kilogram of the body weight of the subject. The increased effective amount may be in a range of 1.05-540 mg/kg, preferably 15-420 mg/kg, more preferably 25-270 mg/kg. The subject may be administered with the increased dosage for a longer period (e.g. one more week, 2 more weeks, or 2 more months) than the duration prescribed with the initial effective amount.

In some embodiments, the mutation in the biomarker is detected before administering the pharmaceutical composition to identify subjects predisposed to the disease. For example, subjects with a BRCA1 germline mutation are at a higher risk of contracting breast cancer, or ovarian cancer.

In some embodiments, the biomarkers are measured/detected after each administration.

For example, the measurement may be 1-5 minutes, 1-30 minutes, 30-60 minutes, 1-2 hours, 2-12 hours, 12-24 hours, 1-2 days, 1-15 weeks, 15-20 weeks, 20-30 weeks, 30-40 weeks, 40-50 weeks, 1 year, 2 years, or any period of time in between after the administration.

In some embodiments, the administration is stopped once the subject is treated.

In an embodiment, the present disclosure also provides a method of treating a bacterial infection by administering to the subject an effective amount of the antibacterial composition in a subject. In some embodiments, the subject is a mammal having a bacterial infection. In some embodiments, the subject is a human. The antibacterial composition includes the medicinal nanocomposite. The antibacterial composition may further comprise one or more pharmaceutically acceptable carriers as described above. In some embodiments, the antibacterial composition has a minimum inhibitory concentration (MIC) of 0.1 to 3.5 mg/ml, preferably 0.2 to 3 mg/mL, preferably 0.3 to 2.5 mg/mL, preferably 0.3 to 2.25 mg/mL, preferably 0.4 to 2 mg/mL, preferably 0.5 to 1.75 mg/mL, preferably 0.6 to 1.5 mg/mL, preferably 0.7 to 1.4 mg/mL against a bacterial strain selected from the group consisting of *Pseudomonas aeruginosa* and *Staphylococcus aureus*.

The examples below are intended to further illustrate protocols for the preparation and characterization of the medicinal nanocomposite as well as the methods of treating cancer and bacterial infection and are not intended to limit the scope of the claims.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

EXAMPLES

Materials and Methods

Figure 3A:
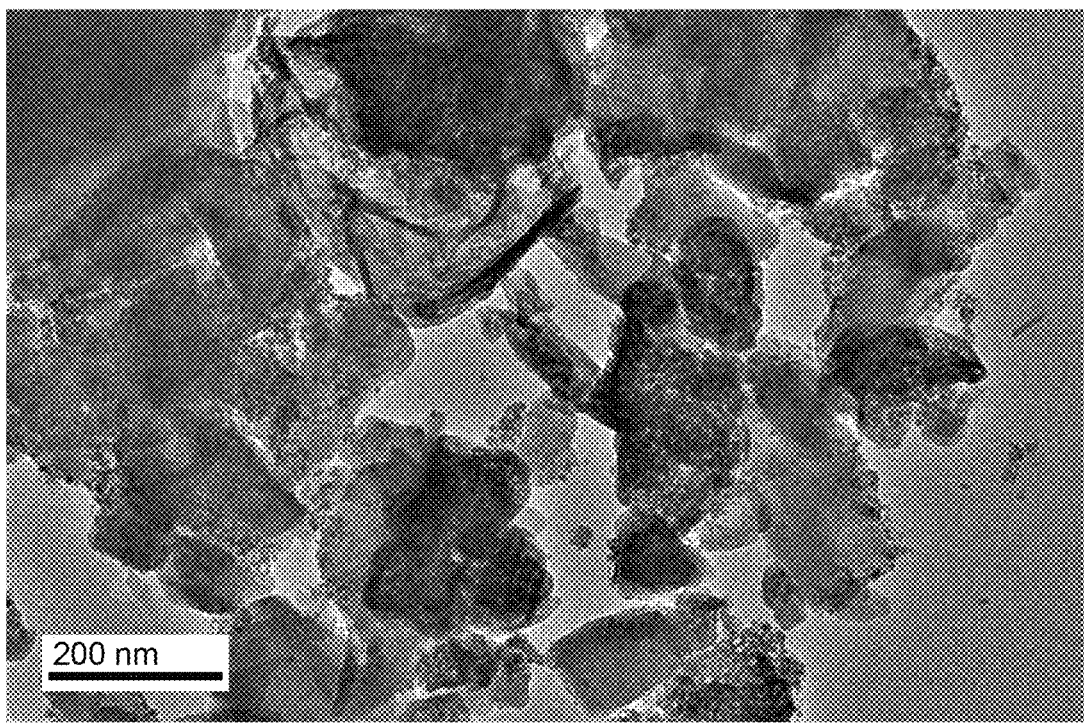
FIGS. 3A and 3B show Transmission electron microscopy (TEM) images of TiZSM, according to certain embodiments.
Figure 3B:
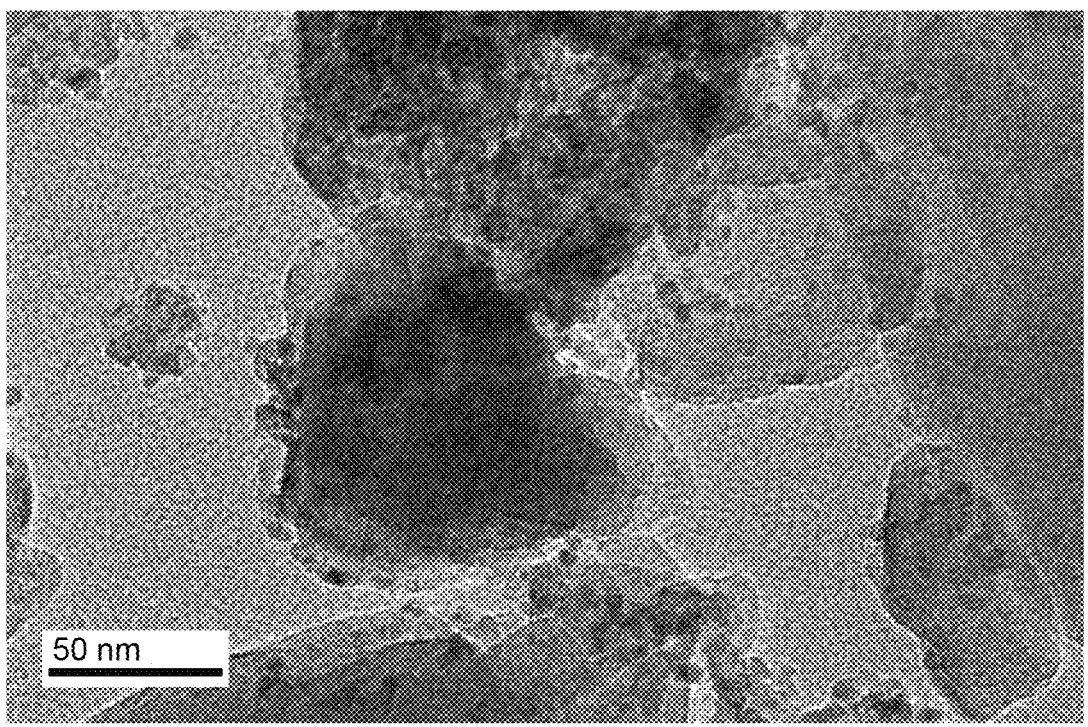

Silver nitrate ($AgNO_3$, American Chemical Society (ACS) grade), ≥99%) and cisplatin ($Pt(NH_3)_2Cl_2$] crystalline) were purchased from Sigma Aldrich. Supsil™ Standard Silica (80 nm) in monodispersed spherical form was purchased from Superior silica, USA. Structured silica like SBA-16 was prepared using a sol-gel technique. Pluronic F127 (Sigma Aldrich) was used as a template. Further, tetraethyl orthosilicate ($SiC_8H_{20}O_4$, Sigma Aldrich, reagent grade, 98%) was used as a silica source. TiZSM-5 was obtained using titanium isopropoxide ($C_{12}H_{28}O_4Ti$), and tetrapropyl ammonium bromide template (TPABr) template, using a hydrothermal technique. Representative TEM images of TiZSM-5 particles are shown in FIGS. 3A and 3B.

Preparation of the Porous Silicate Material.

Figure 4:
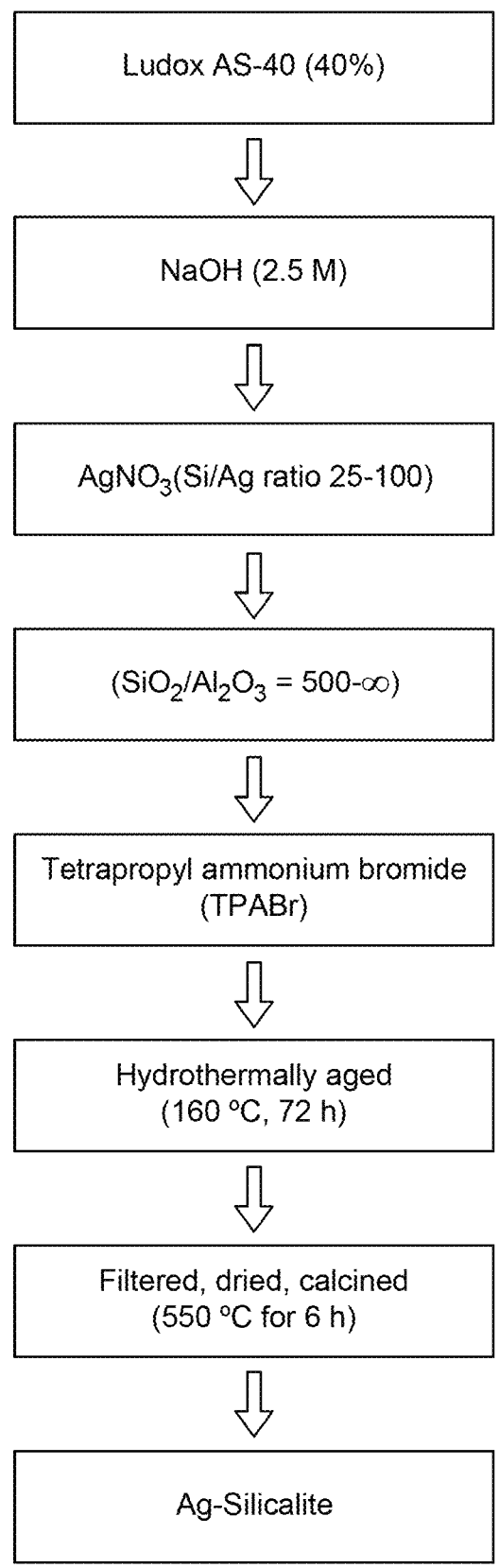
FIG. 4 is an exemplary flow diagram of preparation of the porous silicate material, according to certain embodiments.

Referring to FIG. 4, an exemplary flow diagram of preparation of the porous silicate material is illustrated. 11.42 g of Ludox® AS-40 was taken and mixed with 8 g of tetrapropyl ammonium hydroxide (TPAOH, $C_{12}H_{29}NO$, 40%) for 1 h. Further, 0.31 g of sodium fluoride (NaF, F/Si ratio 1), 0.63 ml of titanium isopropoxide and 0.96 g of aluminium nitrate ($Al(NO_3)_3$) was added and stirred for 30-60 minutes, to which 0.93 g of NaOH dissolved in 9 ml water was added dropwise and stirred overnight to form a solution. The solution was transferred in 250 ml autoclave bomb and kept in static oven hydrothermally treated at 160° C. for 72 h. A powder was recovered by filtration, drying and calcination (550° C. for 6 h). Silicalite was synthesized using TPABr and Ludox as silica source. Silicalite was further changed to mesosilicalite using Cetyltrimethylammonium bromide (CTAB, $C_{19}H_{42}BrN$) template.

Preparation of 1-6 wt. % Ag/MSS for Antibacterial Study

For 1 wt. % Ag loading, 0.016 g of silver nitrate was dissolved in 30 ml distilled water for 30 minutes. 1.0 g of pre-dried MSS was added to form the aged mixture. Further, the aged mixture was allowed to stir for 12 h. The aged mixture was further heated at 120° C. for 6 h to form the first product. The first product was powdered using a mortar and pestle and finally calcined at 500° C. for 3 h to form the second product, that is, 1 wt. % Ag/MSS. Similarly, 2 wt. % (0.031 g), 4 wt. % (0.063 g) and 6 wt. % (0.094 g) Ag was loaded over MSS (1 g) and further calcined to obtain the Ag/MSS.

Preparation of 1-6 wt. % Ag/MSS or Structured Silica/Cisplatin

Cisplatin (CP) (~30 mg) was added in a normal saline solution (10 ml) and further mixed for dissolution for 20 minutes. 1-6 wt. % Ag/MSS samples (600 mg) were further added to form a solution and were stirred overnight in an ice cool environment. The solution was filtered, washed and dried. The filtrate was then analyzed by UV-visible spectroscopy at 208 nm.

Characterization Techniques

Phases of 1-6 wt. % Ag/MSS and 4 wt. % Ag/structured silica were analyzed using benchtop XRD (Miniflex 600, Rigaku, Japan). Textural features including a Brunauer-Emmett-Teller (BET) surface area, a pore size and a pore volume was measured using nitrogen adsorption technique (ASAP-2020 plus, Micromeritics, USA). The silver nanoparticle chemical coordination was analyzed using Differential Reflectance Spectroscopy-Ultraviolet (DRS-UV-visible) spectroscopy analysis (JASCO, Japan). The hydrodynamic particle size, polydispersity index and zeta potential of Ag/MSS/Pt sample was measured by Zetasizer Nano ZS (Malvern, UK). The sample was mixed with Milli-Q water in the ratio of 1:2 and sonicated for 30 minutes. The sample was then transferred into disposable measuring cell and analyzed. The measurement was carried out three times at room temperature. Scanning electron microscope (SEM) was analyzed using JSM-6610LV from JEOL. Elemental mapping was obtained by energy dispersive spectroscopy (EDS) using Aztec software (Oxford).

In Vitro Cisplatin Release Experiment

Figure 5:
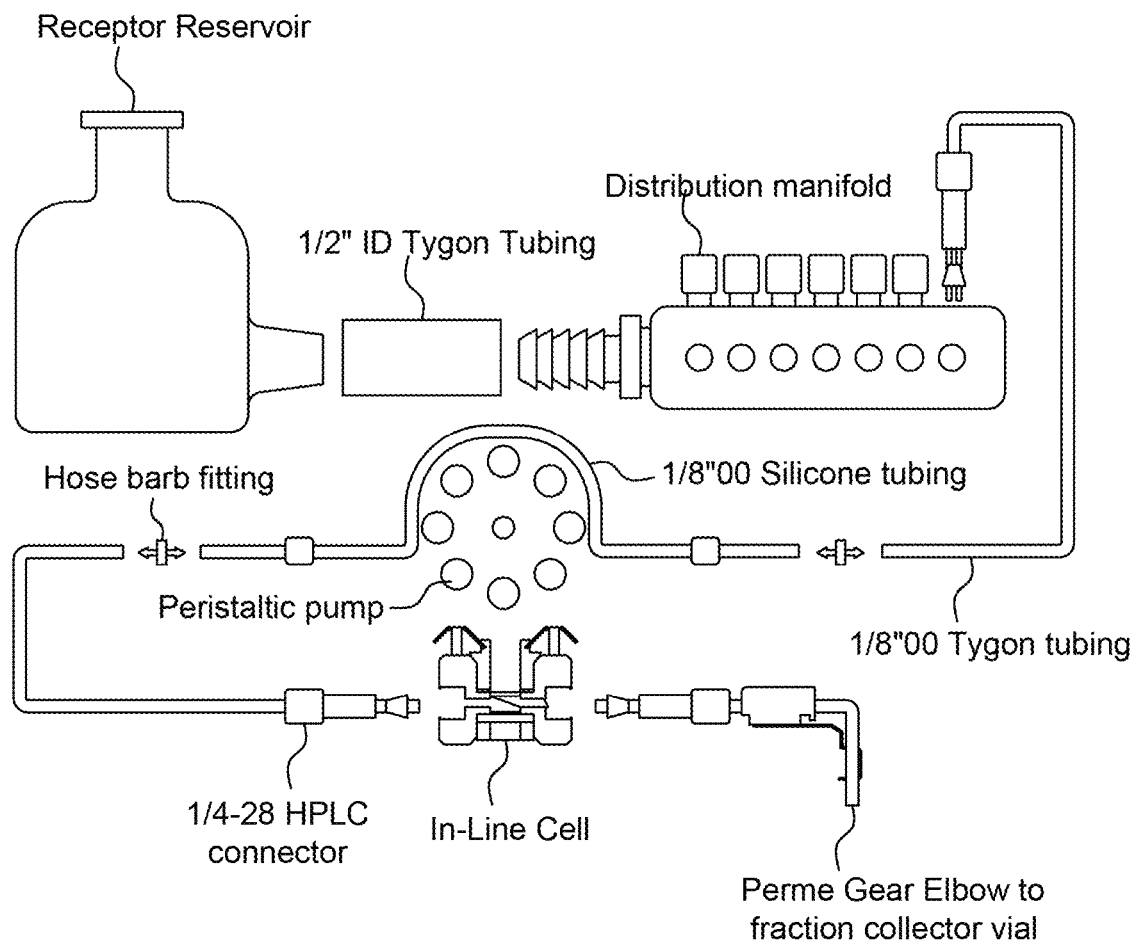
FIG. 5 is a schematic diagram of an automated diffusion cell system equipped with a flow type Franz cell, according to certain embodiments.

A drug release analysis of 1-6 wt. % Ag/MSS and 4 wt. % Ag loaded SBA-16, TiZSM-5, mesosilicalite, halloysite and Ag-silicalite was studied by Franz cells (PermeGear, USA). 1-6 wt. % Ag/MSS and 4 wt. % Ag loaded SBA-16, TiZSM-5, mesosilicalite, halloysite and Ag-silicalite are collectively referred to as 'the nano formulations or nanomaterials' or individually referred to as 'the nano formulation or nanomaterial' unless otherwise specified. A system was assembled with a tumor acidic solvent reservoir, 8 in-line cells, a solution driving peristaltic pump and a sample collector. The setup was constantly maintained at 37° C. using water heater (Julabo GmbH). A dialysis membrane (molecular weight cut-off (MWCO)=14000, Sigma) was activated by washing in a phosphate buffer saline solution (PBS). Air blockages in tubings were removed by purging with the PBS. One square inch sized dialysis membrane was placed inside the Franz cells. The Ag loaded nano formulation was mixed with the PBS solution (30 mg/ml) and further placed in a donor site (FIG. 5). Further, the PBS solution was pumped at a constant flow rate of 10 ml/h with volume to time ratio 0.167. Samples collected at every hour was analyzed and quantified by cisplatin calibration curve using Japan Spectroscopic Company (JASCO Ultraviolet-Visible) spectroscopy. The drug release study using each nano formulations were studied in triplicate.

In Vitro Cell Culture

Two cancer cell lines, namely, HCT-116 and HeLa were considered to study the impact of samples (medicinal nanocomposite) on viability and proliferation of such cell lines. A non-cancer cell line, embryonic kidney cells (HEK-293), was considered as a control cell line. HCT-116, HeLa and HEK-293 are collectively referred to as 'the cells' or individually as 'the cell' unless otherwise specified. The cells were cultured and maintained in the Dulbecco's Modified Eagle Media (DMEM), L-glutamine (5%), penicillin (1%), streptomycin (1%), Fetal bovine serum (FBS) (10%), and selenium chloride (1%). The cells were grown in 96 well plates in a 5% $CO_2$ incubator (Thermo Fisher Scientific, Inc., Waltham, MA, USA) at 37° C., and 75-80% confluence cells and the cells processed for further assay.

3-(4,5-dimethylthiazol-2-yl)-2,5-diphenyltetrazolium bromide (MTT) Assay

A MTT assay is a colorimetric assay for measuring cell metabolic activity. The MTT assay is based on the ability of nicotinamide adenine dinucleotide phosphate (NADPH)-dependent cellular oxidoreductase enzymes to reduce the tetrazolium dye MTT to insoluble formazan, which has a purple colour. 70-80% confluence cells were treated with various doses (5.0 microgram (µg) to 50 µg/ml) of MSS, 1 wt. % Ag/MSS, 2 wt. % Ag/MSS, 4 wt. % Ag/MSS, 6 wt. % Ag/MSS, Ag-silicalite, and cisplatin (CP). In control group, MSS, 1 wt. % Ag/MSS, 2 wt. % Ag/MSS, 4 wt. % Ag/MSS, 6 wt. % Ag/MSS, Ag-silicalite, and CP were excluded and after 48 hours, the cells were incubated in MTT (Sigma-Aldrich, St. Louis, MO, USA) for 4 hours.

In control and nano formulation treated cells, MTT (5 mg/ml) was added, and the cells were further incubated in a $CO_2$ incubator for 4 hours. Further, the cell culture media was replaced with dimethyl sulfoxide (DMSO) (1%), and the 96-well plate was further examined under an enzyme-linked immunoassay (ELISA) plate reader (Biotek Instruments, USA) at a wavelength of 570 nm. The percentage of cell viability was calculated for a statistical analysis. ANOVA were used to analyze the data. All the analysis was run on GraphPad Prism software. P value less than 0.05 was taken as significant difference in results.

Apoptotic DAPI (4',6-diamidino-2-phenylindole) Staining Assay

DAPI is a fluorescent dye used to distinguish between live and dead cells. In live cells, the dye pass through a membrane less effectively. Therefore, the DAPI staining assay is an effective marker to identify the cell viability based on the cell structural changes. The morphology changes of cancer nuclear structure due to treatments of MSS, 1 wt. % Ag/MSS, 2 wt. % Ag/MSS, 4 wt. % Ag/MSS, 6 wt. % Ag/MSS, Ag-silicalite, and CP were examined by the DAPI staining assay. Cells were divided into two groups such as a control group and an experimental group. The control group was without nano formulation and CP treatments. In the experimental group, 1 wt. % Ag/MSS, 2 wt. % Ag/MSS, 4 wt. % Ag/MSS, 6 wt. % Ag/MSS, Ag-silicalite, and CP (25 µg/ml) were added.

Post 48-hour treatment, the control and experimental groups were exposed to ice-cold (4%) paraformaldehyde and further with Triton X-100 in the PBS solution. The cells were stained with DAPI (1.0 µg/ml) for 5 minutes under a dark environment, and the cells were finally washed with the PBS solution and cover slipped. A deoxyribonucleic acid (DNA) staining was examined by using confocal scanning microscope (Zeiss, Germany). The data presented as mean (±) standard deviation (SD) obtained from triplicates and one-way ANOVA followed by Dennett's post hoc test with GraphPad Prism Software (GraphPad Software, USA) for final statistical analysis.

Antibacterial Activity

Bacterial strains of *Pseudomonas aeruginosa* ATCC27853 (gram-negative) and *Staphylococcus aureus* ATCC25923 (gram-positive) were subjected to antibacterial studies. The bacteria were sub-cultured and maintained on Mueller Hinton Agar (MHA). A stock solution of the nanomaterial (8 mg/ml) was sonicated for 10 minutes in Mueller Hinton Broth (MHB) to obtain a homogenized solution for an antibacterial assay. Inoculum was prepared by adjusting the cell number to $1.5 \times 10^8$ colony forming unit per milliliter (CFU per ml) by using freshly grown strains, grown overnight at 37° C.

Broth Dilution Method

A minimum inhibitory/bactericidal concentration (MIC/MBC) of the synthesized nanomaterial was obtained by applying a broth dilution method. 1 ml of sterile MHB with the varying concentration of nanomaterial starting from 8 mg/ml to 250 µg/ml was formulated except $AgNO_3$ (0.125 to 0.0038 mg/ml). About 100 µL of adjusted inoculum was inoculated into each tube and were further incubated for 24 h (at 37° C.) with agitation of 120 rotations per minute (rpm).

A control tube of bacteria, also referred as control, had no nanomaterial. 10 µL extracted from the tubes were put on prepared MHA plates and further incubated at the same conditions. After the completion of incubation duration, the MHA plates were recorded for MIC and MBC values. MIC was taken as the lowest concentration of nanomaterial that inhibited 90% of the bacterial growth. However, MBC was recorded as the lowest concentration that killed the bacterial cells or had CFU less than three. The data is presented as mean standard deviation obtained from triplicates and one-way ANOVA followed by Dennett's post hoc test with GraphPad Prism Software, USA for final statistical analysis.

Results

Figure 6A:
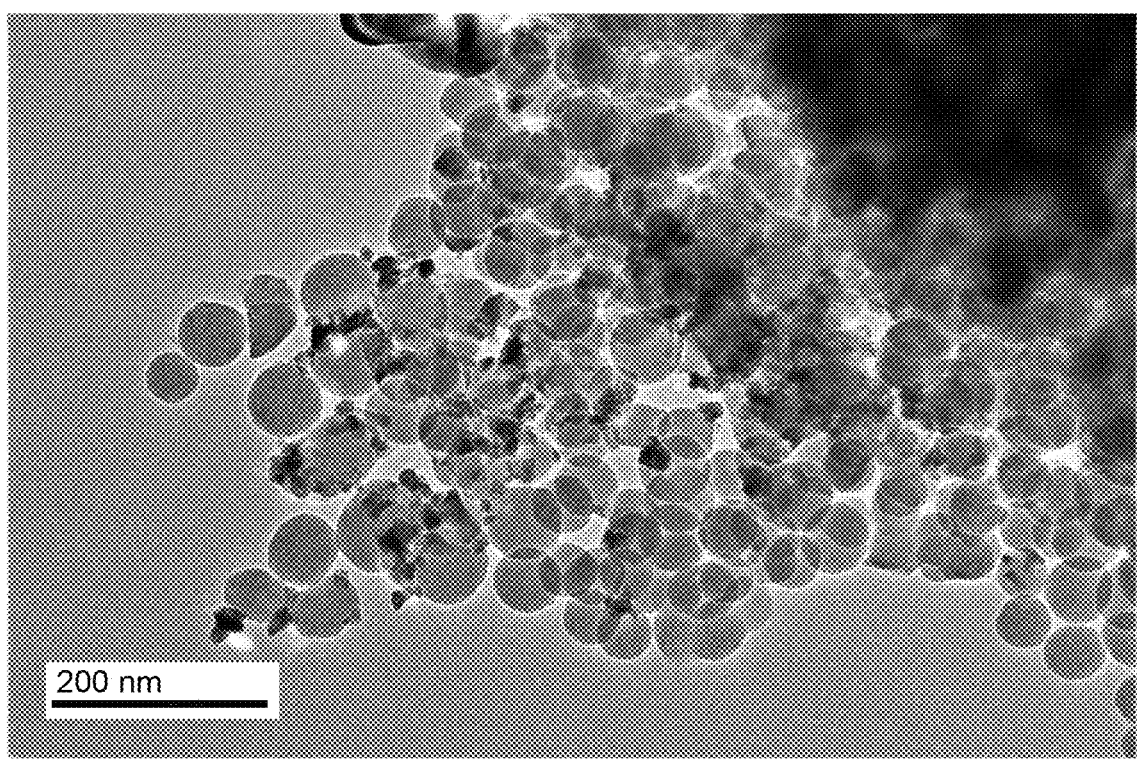
FIG. 6A shows TEM image of silver loaded monodispersed spherical silica (Ag/MSS), according to certain embodiments.
Figure 6B:
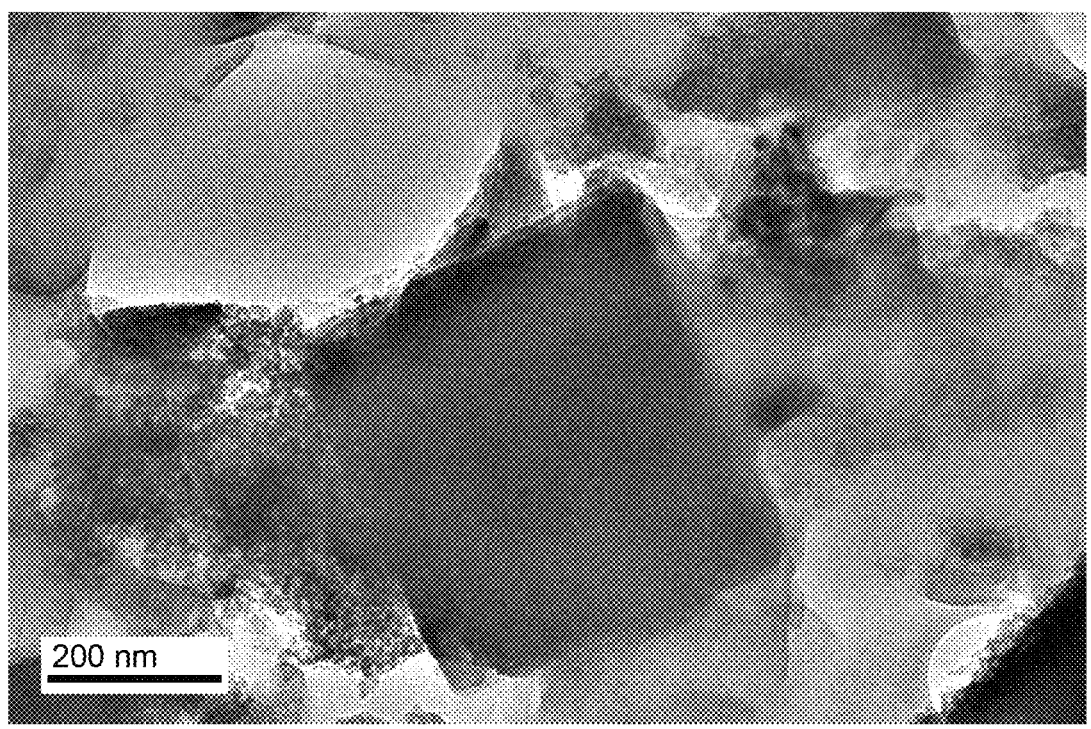
FIGS. 6B and 6C show TEM images of cisplatin functionalized Ag-silicalite, according to certain embodiments.
Figure 6C:
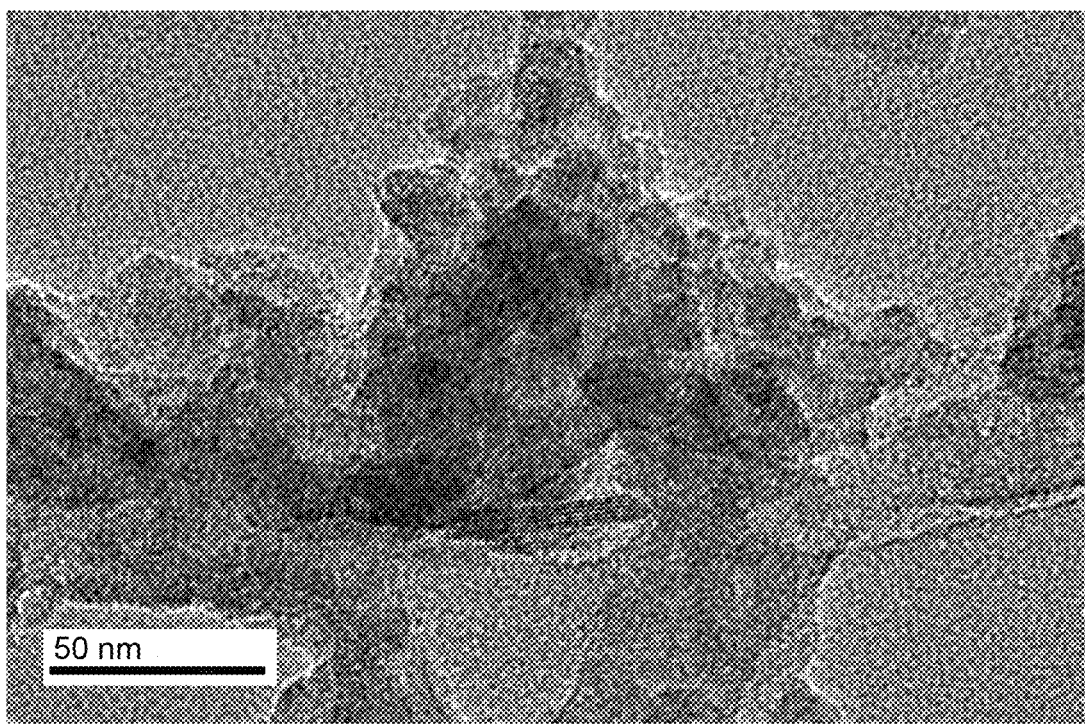

Referring to FIG. 6A, a TEM image of 6 wt. % Ag/MSS is depicted. The observed particle distribution of Ag NPs on the silica confirms less aggregation and correlated with the size of 80 nm. TEM images of cisplatin functionalized Ag-silicalite showed particle size in a range of 50 nm-200 nm (FIGS. 6B and 6C).

Figure 7A:
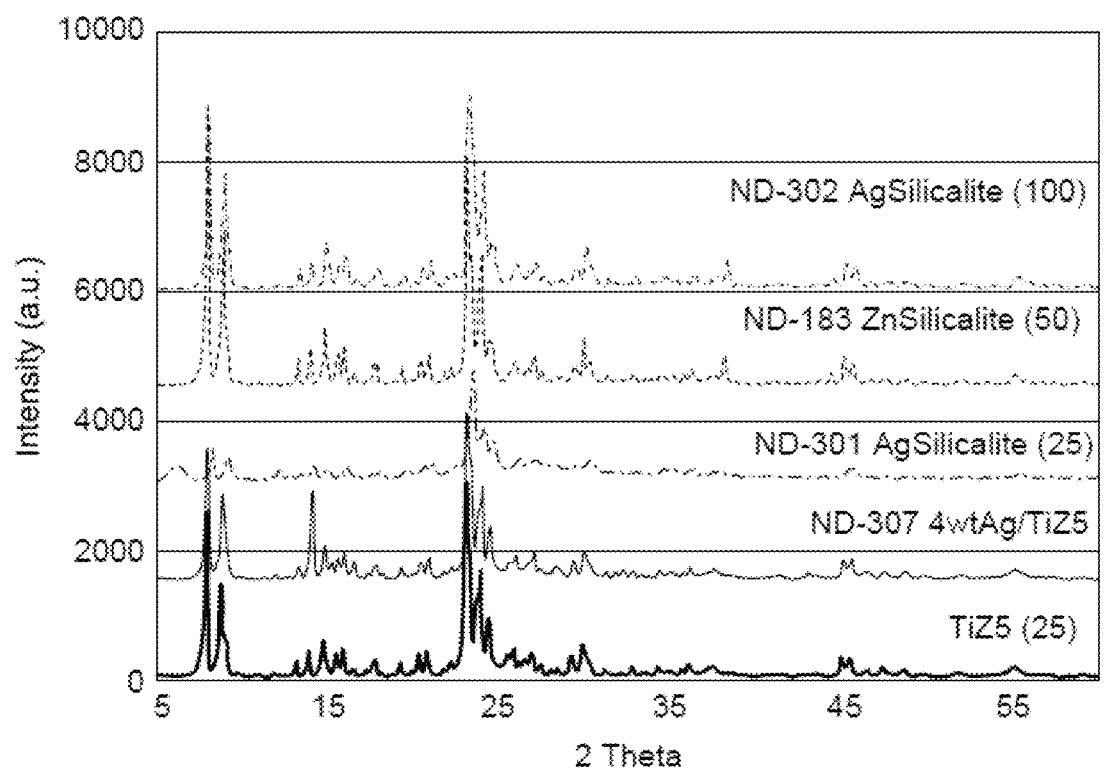
FIG. 7A shows X-Ray Diffraction (XRD) images of various porous silicate materials is provided, namely, TiZ5, 4 wt. % Ag/TiZ5, Ag silicalite, Zn silicalite, and Ag silicalite, according to certain embodiments.

Referring to FIG. 7A, XRD images of various porous silicate materials is provided, namely, (a) TiZ5, (b) 4 wt. % Ag/TiZ5, (c) Ag silicalite, (d) Zn silicalite, and (e) Ag silicalite, are provided.

Figure 7B:
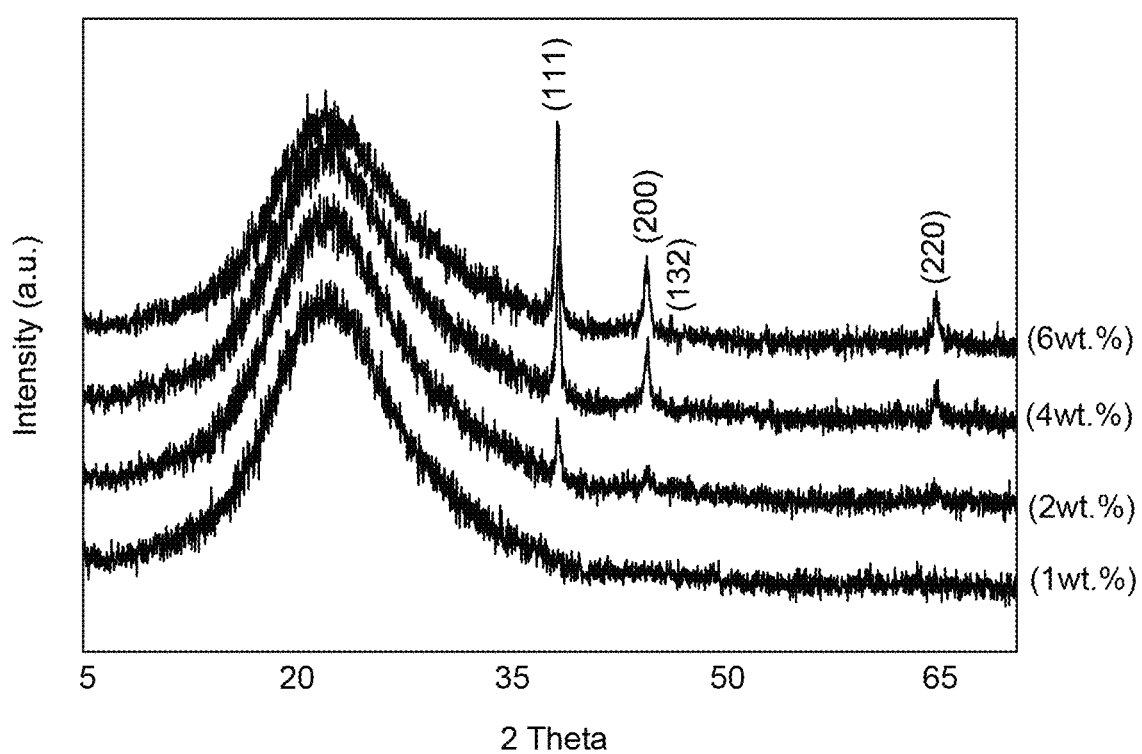
FIG. 7B shows XRD images of Ag/MSS, of various weight percentages, according to certain embodiments.

Referring to FIG. 7B, XRD images of 1-6 wt. % Ag loaded MSS, namely, (a) 1 wt. % Ag/MSS, (b) 2 wt. % Ag/MSS, (c) 4 wt. % Ag/MSS and (d) 6 wt. % Ag/MSS, respectively, are illustrated. From the FIG. 7B, it can be observed that the 1 wt. % Ag/MSS showed only broad diffraction pattern characteristics to that of amorphous silica. With 2 wt. %, 4 wt. % and 6 wt. % loadings, Ag nanoparticles corresponding to cubic phase were observed with (111), (200) and (220) plane. A phase related to AgO species (132) is observed at 6 wt. % loadings.

Zeta potential measurement confirmed a colloidal state stability of nanoparticles. 4 wt. % Ag/MSS/Pt sample was analyzed using Zeta potential. The particle size curve shows distributed in the range between 70-100 nm. Peak maxima occur at 78.2 nm. The zeta potential of 4 wt. % Ag/MSS (−5.6 millivolt (mV)) with polydispersity value of 0.372 shows that the surface is negatively charged than reported value of silver nanoparticles (Ag NPs) (−1.10 mV) and maintained stability.

Figure 8:
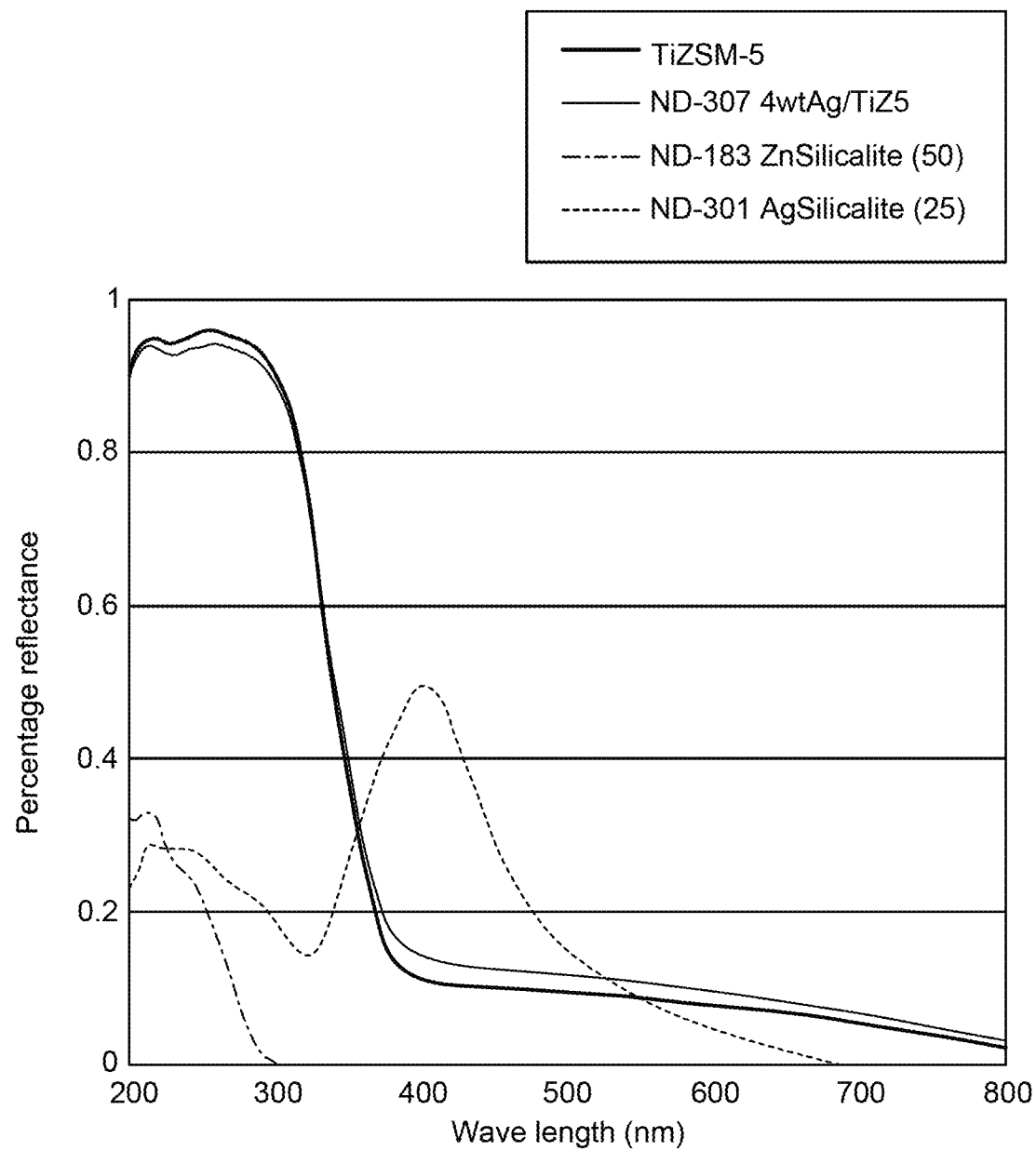
FIG. 8 shows diffuse reflectance spectra of TiZSM-5, 4 wt. % Ag/TiZSM-5, Zn-silicalite, and Ag-silicalite, according to certain embodiments.

Referring to FIG. 8, Diffuse reflectance spectra of (a) TiZSM-5, (b) 4 wt. % Ag/TiZSM-5, (c) Zn-silicalite and (d) Ag-silicalite, is illustrated.

Figure 9C:
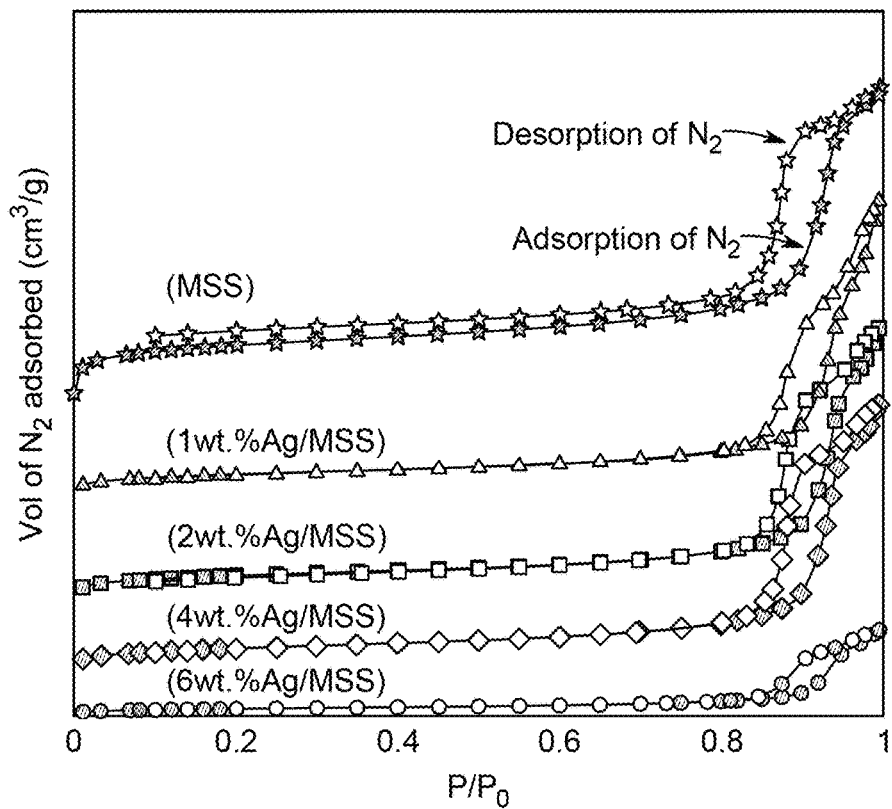
FIGS. 9C and 9D depict $N_2$ adsorption-desorption isotherms and Barrett, Joyner and Halenda (BJH) plot of MSS and Ag loaded MSS, respectively, of varying weight percentages, according to certain embodiments.
Figure 9D:
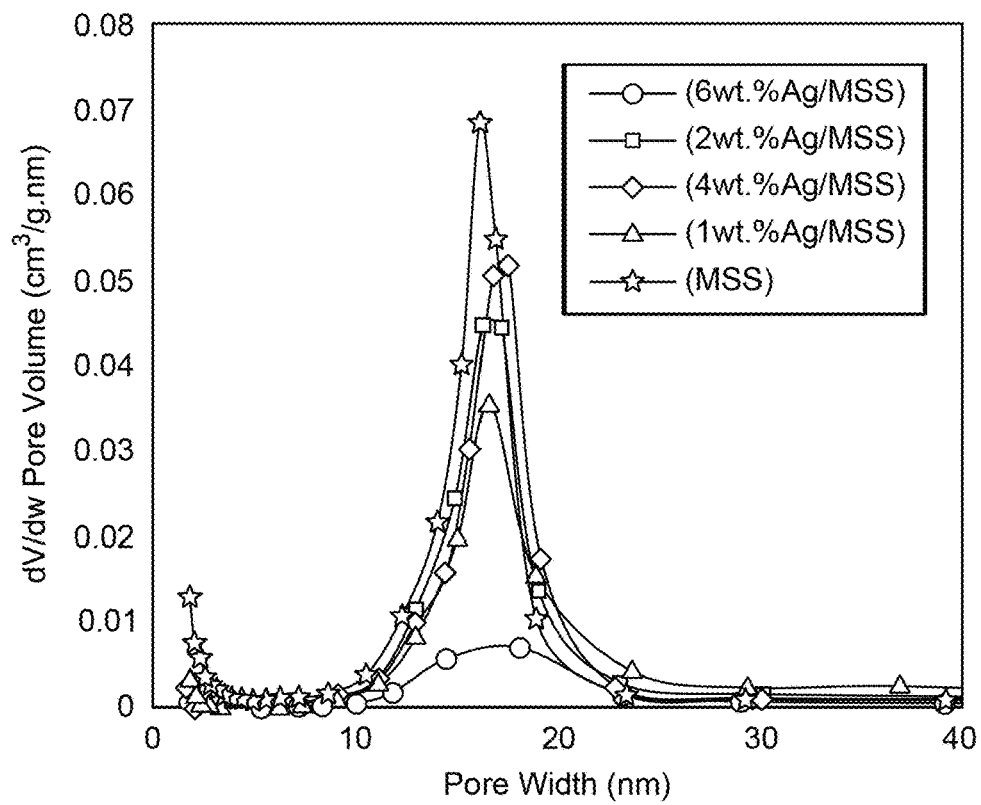
Figure 10A:
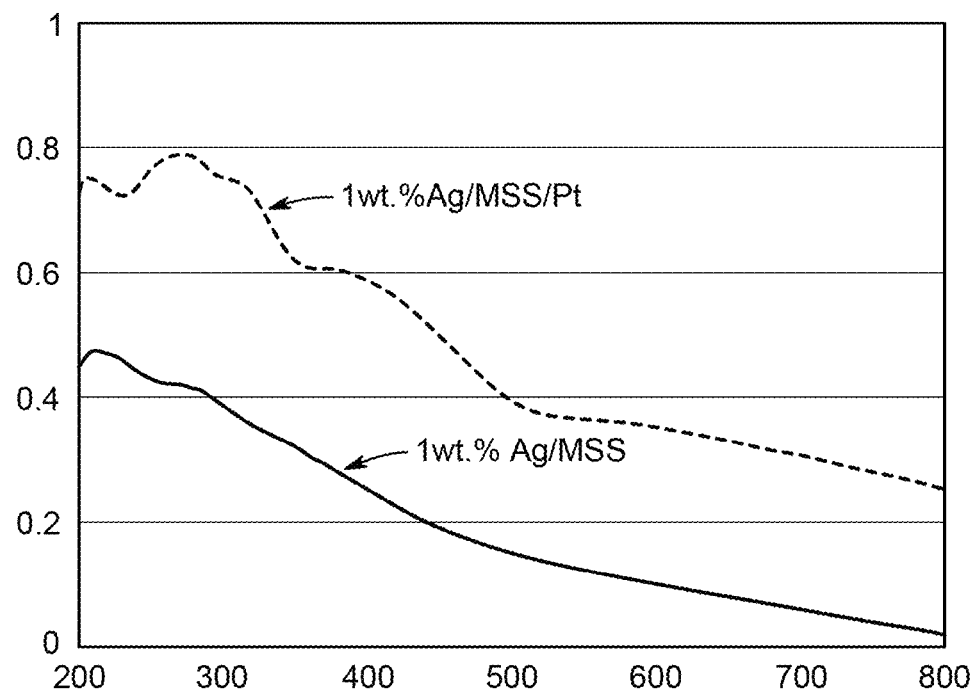
FIGS. 10A-10D are Differential Reflectance Spectroscopy-Ultraviolet (DRS-UV-Visible) spectra of Ag/MSS and Ag/MSS/Pt, of varying weight percentages, according to certain embodiments.
Figure 10B:
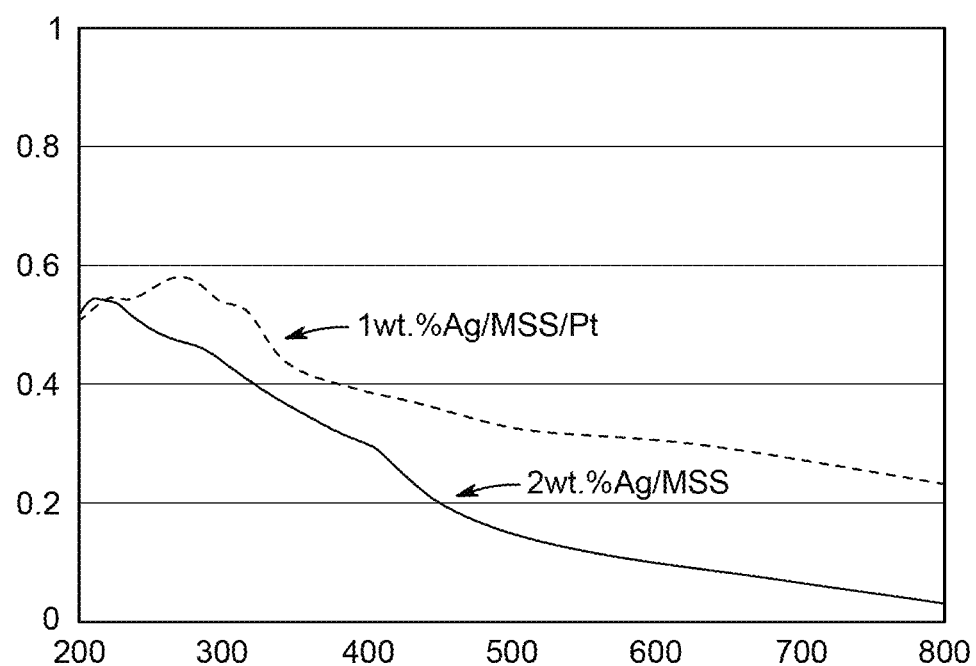
Figure 10C:
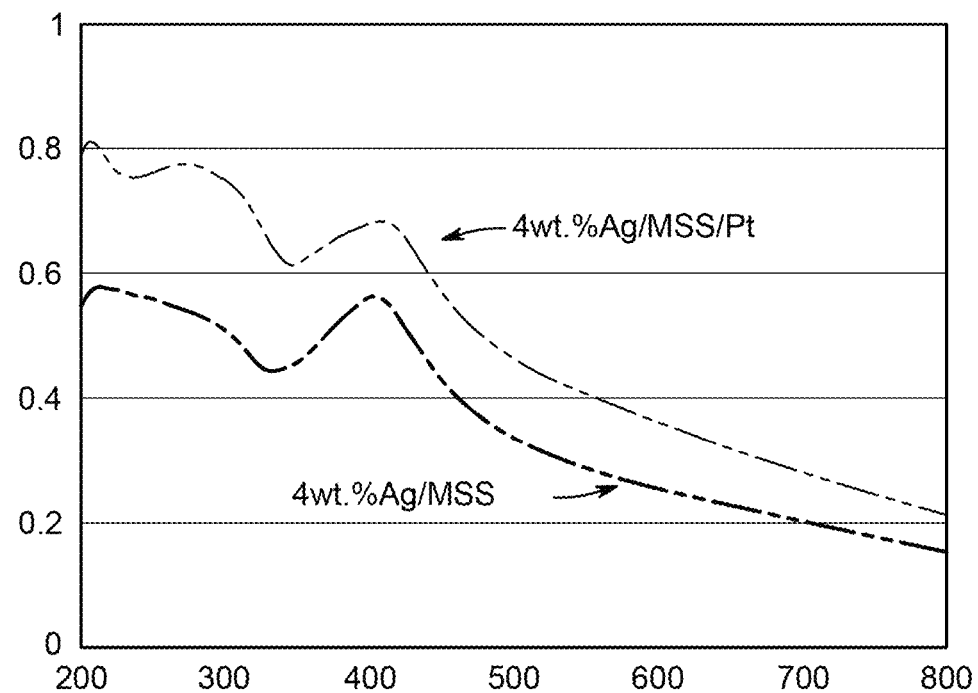
Figure 10D:
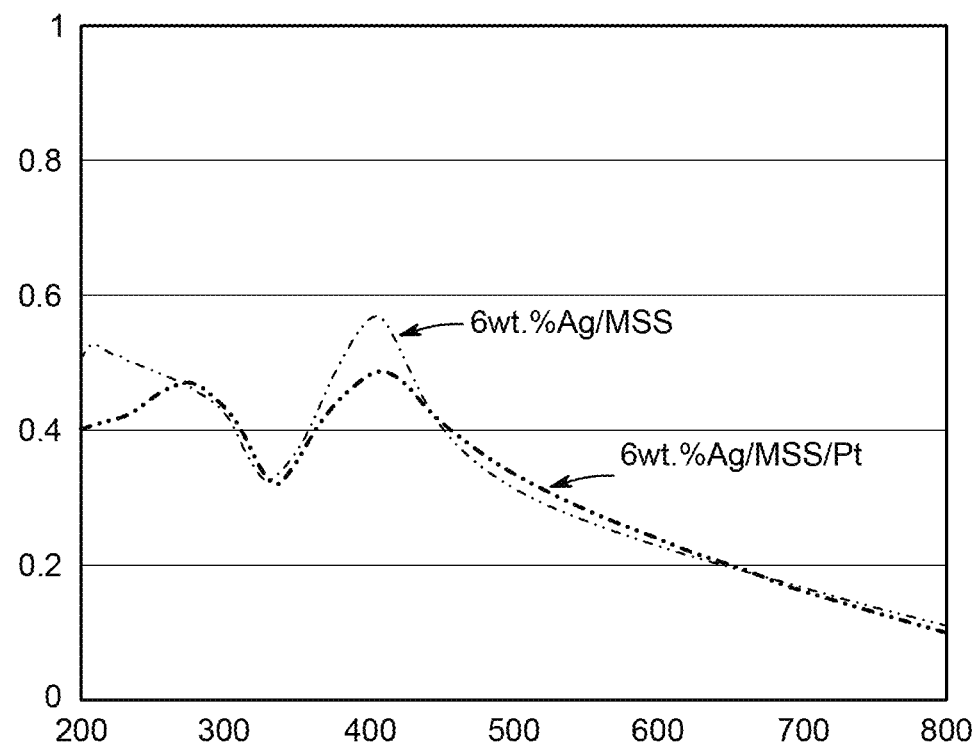
Figure 11A:
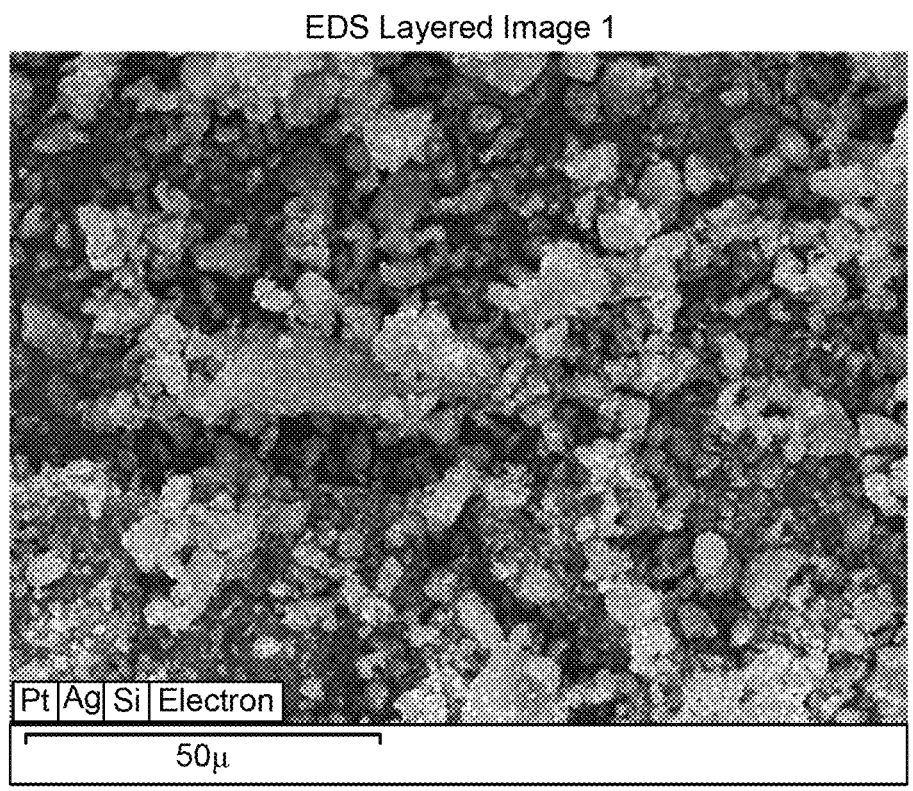
FIGS. 11A-11E are scanning electron microscope-Energy-dispersive X-ray spectroscopy (SEM-EDS) elemental mapping of Si, Ag, Pt elements and EDS spectrum of 1 wt. % Ag/cisplatin/MSS, according to certain embodiments.
Figure 11B:
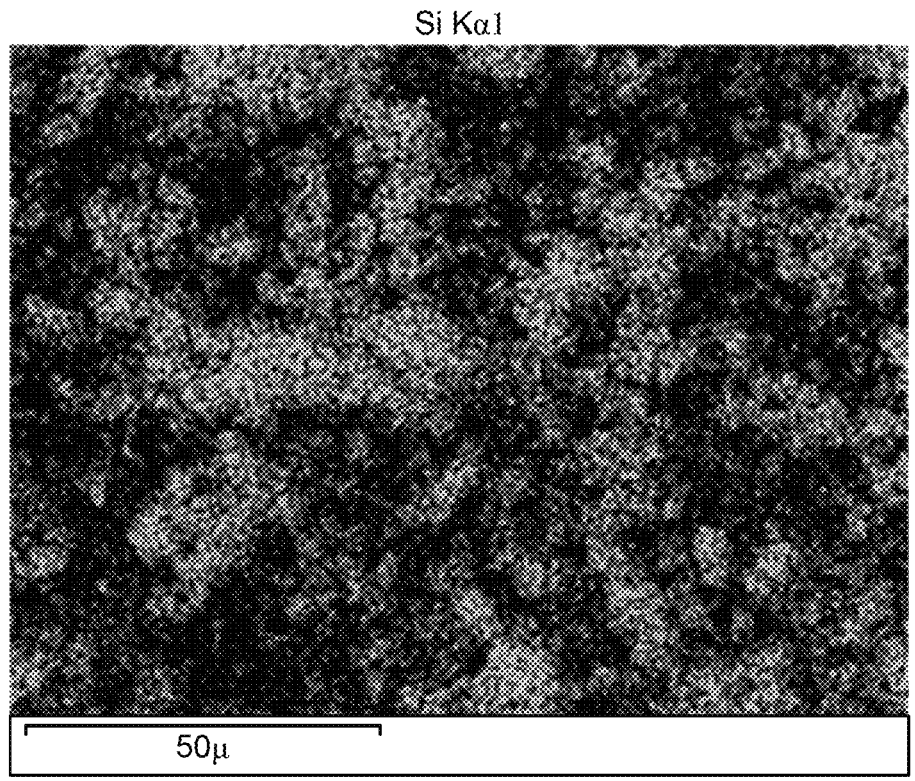
Figure 11C:
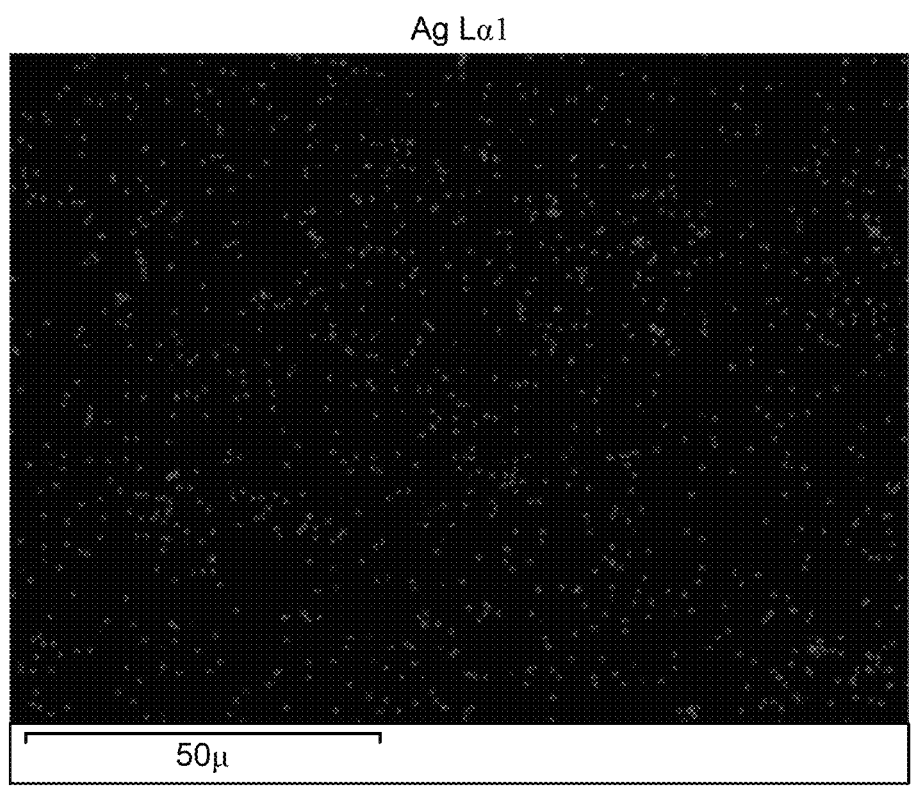
Figure 11D:
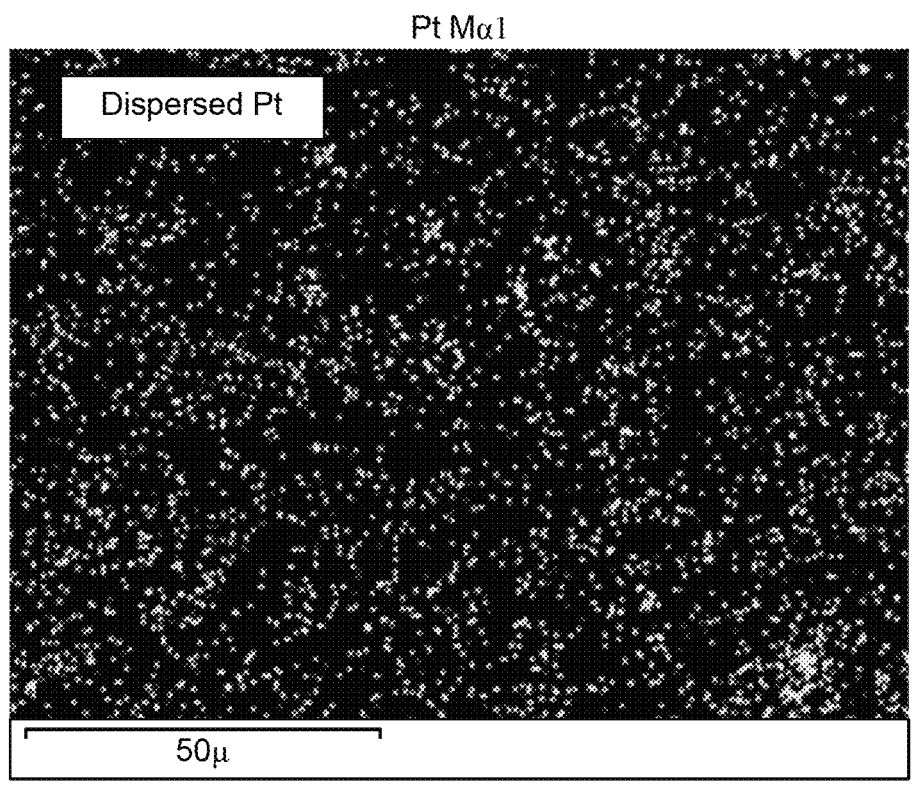
Figure 11E:
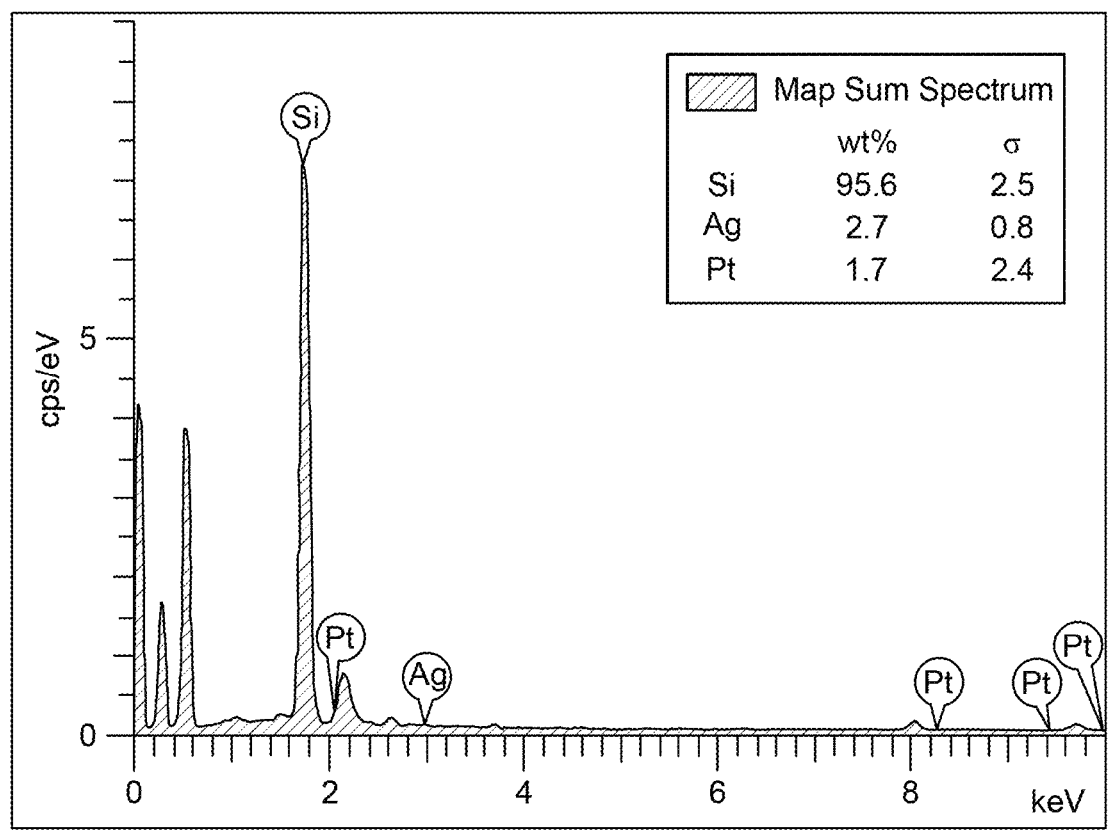
Figure 12A:
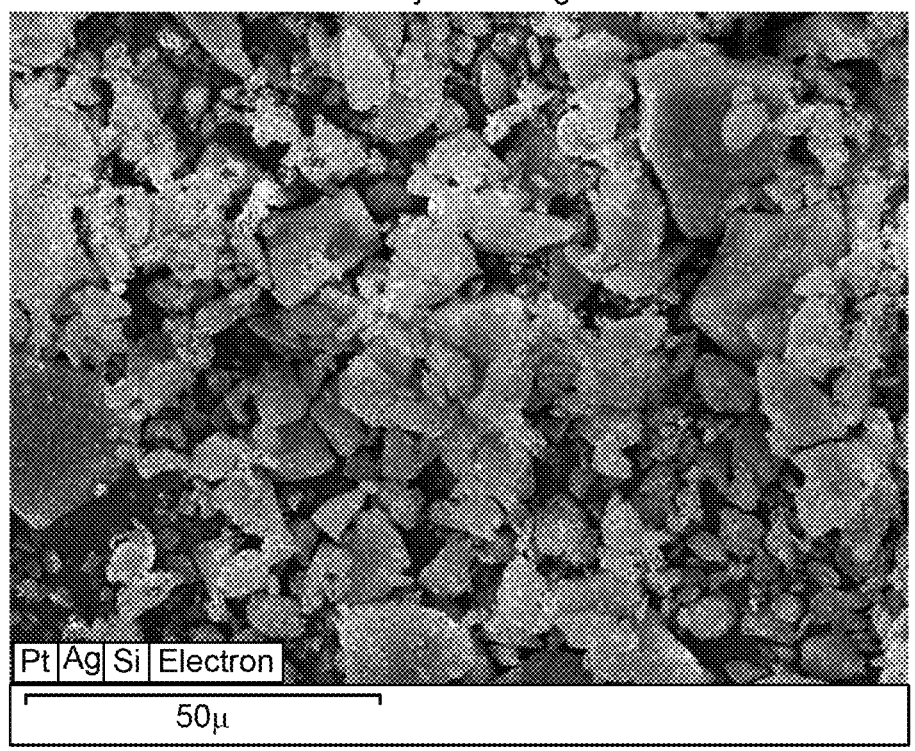
FIGS. 12A-12E show SEM-EDS elemental mapping of Si, Ag, Pt elements and EDS spectrum of 4 wt. % Ag/cisplatin/MSS, according to certain embodiments.
Figure 12B:
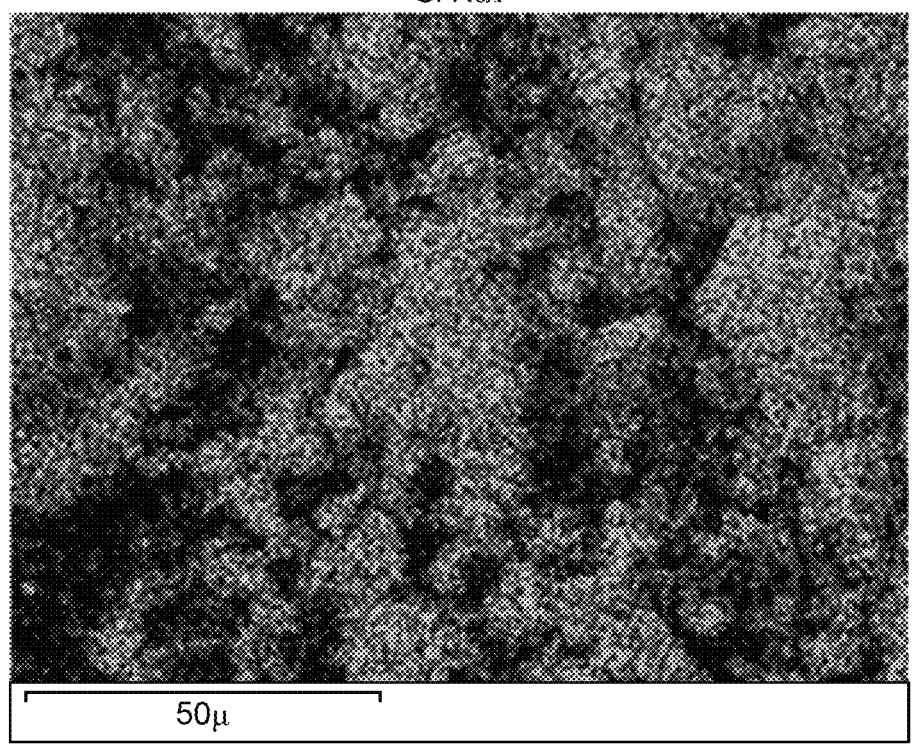
Figure 12C:
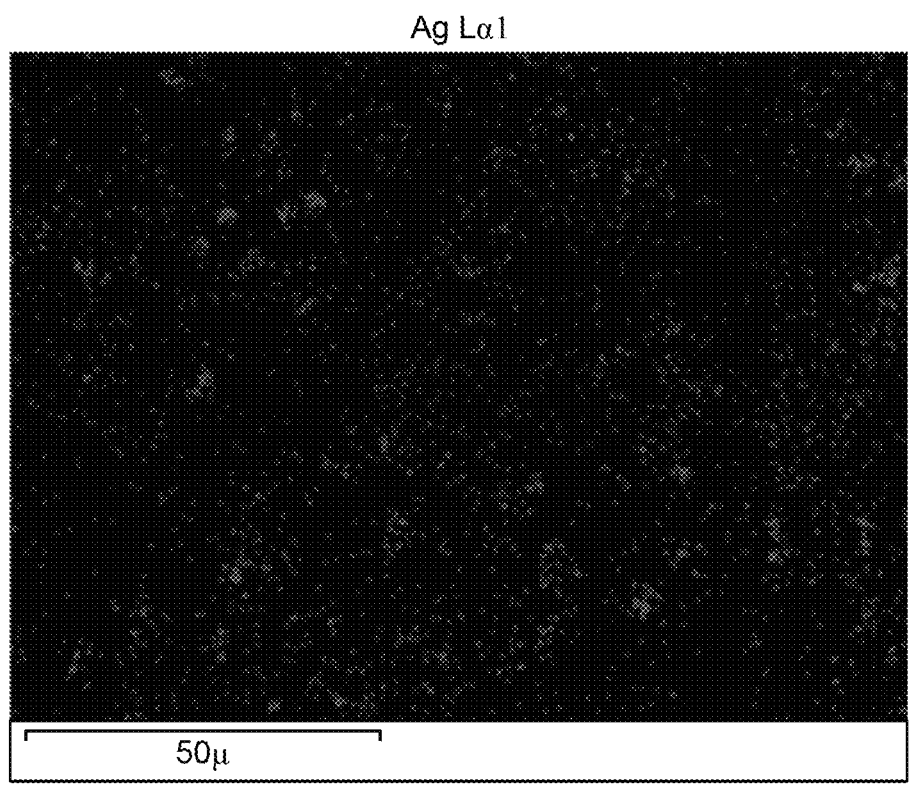
Figure 12D:
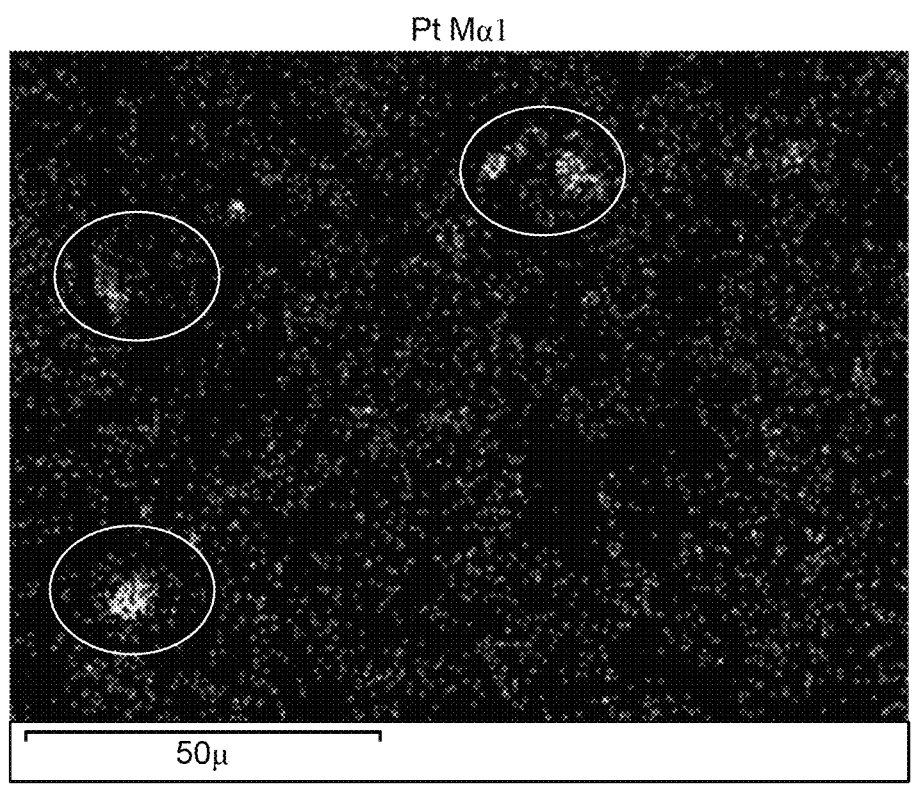
Figure 12E:
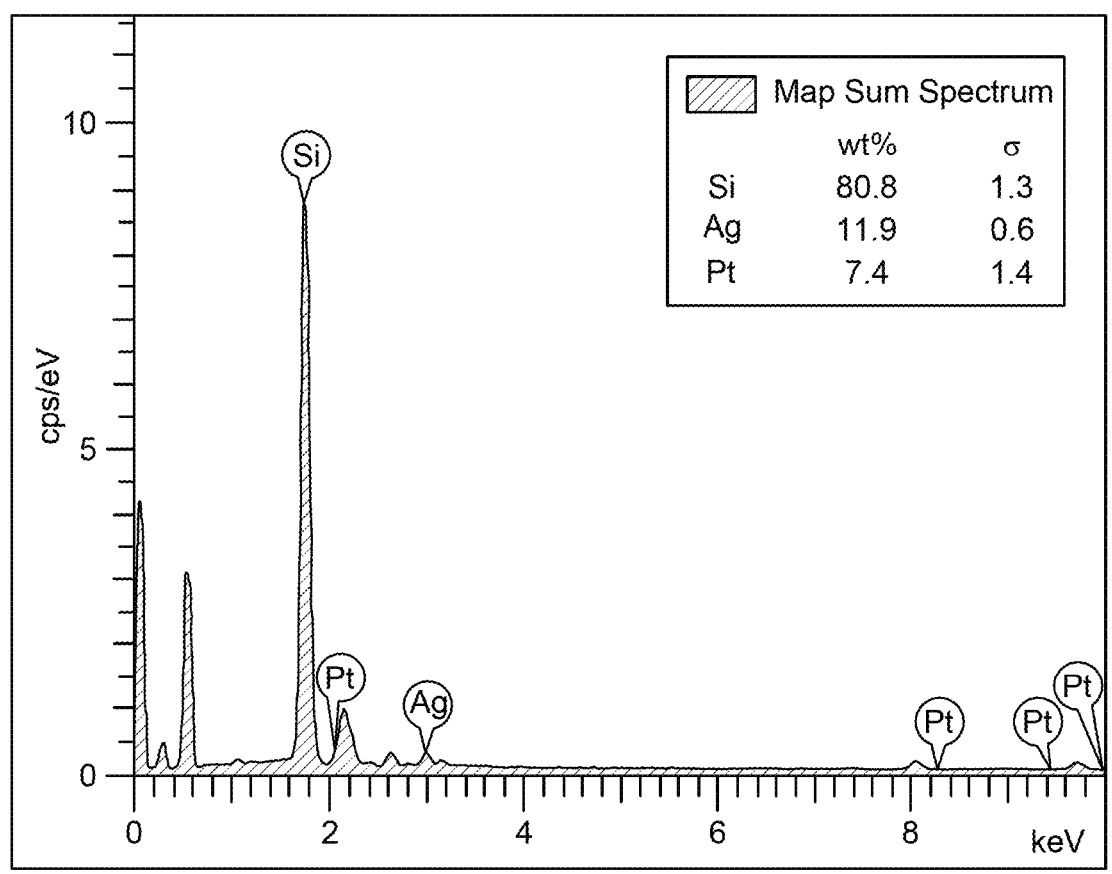

The textural changes with different weight percentage Ag loadings were analyzed by using nitrogen adsorption-desorption technique. FIG. 9A depicts N2 adsorption isotherm of TiZSM-5, 4 wt. % Ag/TiZSM-5, Zn-silicalite, and Ag-silicalite. FIG. 9B depicts a plot of pore width obtained from the N2 adsorption isotherms depicted in FIG. 9A. FIG. 9C-9D depicts N2 adsorption-desorption isotherms and Barrett, Joyner and Halenda (BJH) plot of MSS and Ag loaded MSS, respectively of 1-6 wt. % Ag loaded MSS samples including MSS, 1 wt. % Ag/MSS, 2 wt. % Ag/MSS, 4 wt. % Ag/MSS, and 6 wt. % Ag/MSS. From the FIG. 9C, it can be observed that 1-6 wt. % Ag/MSS samples showed a type IV isotherm with variable hysteresis loop patterns at higher relative pressure $p/p_0 > 0.8$.

From FIGS. 9C-9D it can be observed that 1 wt. % loading of Ag reduced the surface area from 170 $m^2/g$ to 56 $m^2/g$, pore volume showed a slight reduction from 0.35 $cm^3/g$ to 0.28 $cm^3/g$. Pore size distribution showed an increase from 8.3 nm to 20 nm, hence, deposition of Ag at the exterior surface of spherical silica was confirmed. For 2 and 4 wt. % Ag, no significant textural changes are observed. However, 6 wt. % Ag loading over MSS reduced the surface area sharply to 17 $m^2/g$, pore volume to 0.08 $cm^3/g$ with pore size of 20.9 nm. (FIG. 9C).

The coordination effects of different weight percentage concentration of Ag (1-6 wt. % Ag) before and after cisplatin functionalization are illustrated in FIGS. 10A-10D. In the case of Ag/MSS nano formulations, the intensity of bands increases at about 400 nm confirming the presence of Ag nanoparticles. Such a band is primarily attributed due to presence of free electron giving rise to surface plasmon resonance. The presence of a small absorption band at about 253 nm indicates the presence of AgO in MSS. After the introduction of cisplatin, an increase in absorption band at 224 nm, and increased enhancement towards visible region shows the presence of octahedral Pt compounds. The synergistic presence of Pt and Ag nanoparticles confirmed the dispersion and cohabitation of both nanoparticles on MSS. The cisplatin band intensity reduces with increasing Ag content, which confirmed the effective cohabitation of Pt with dominant Ag nanoparticles.

Referring to FIGS. 11A-11E, & 12A-12E, SEM-EDS images depicting elemental mapping of Si, Ag, Pt elements and EDS spectrum of 1 wt. % Ag/cisplatin/MSS and 4 wt. % Ag/cisplatin/MSS, respectively, are illustrated. The Ag and cisplatin distributions of both the samples were mapped using SEM-EDS analysis. From a combined reading of the FIGS. 11A-11E, & 12A-12E, it can be observed that the EDS spectra showed the presence of Si, Ag and Pt elements. The EDX mapping pattern showed well-distributed Ag and Pt species at 1 wt. % loading over MSS. The densification of Ag and Pt species were revealed as Ag loading increases to 4 wt. %. One or more agglomerations were observed which can be attributed to cohabitation of Ag and Pt species leading to formation of large grains.

Figure 13A:
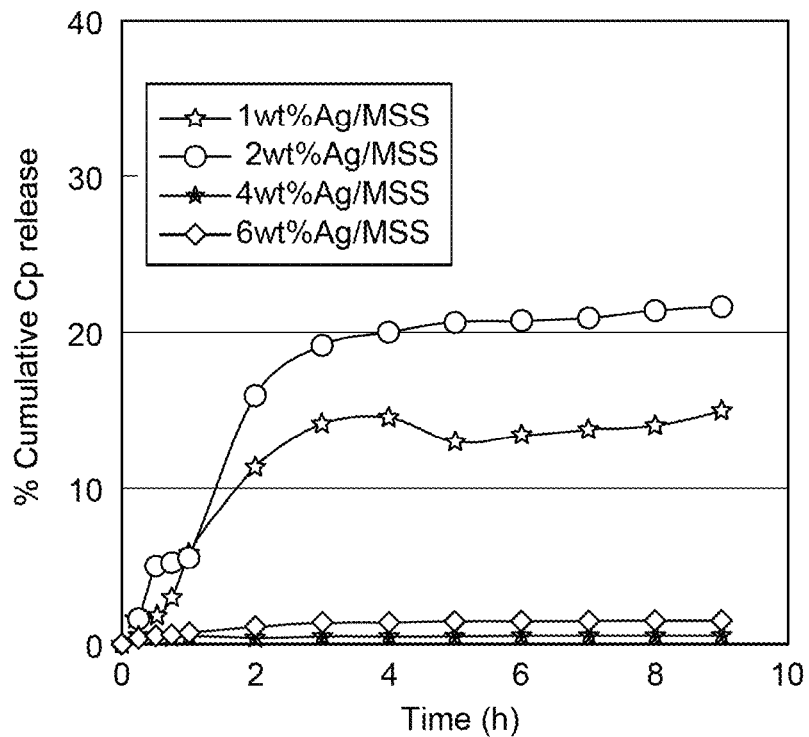
FIGS. 13A-13B depict in vitro cisplatin release study using an automated Franz cell system for 10 hours, according to certain embodiments.
Figure 13B:
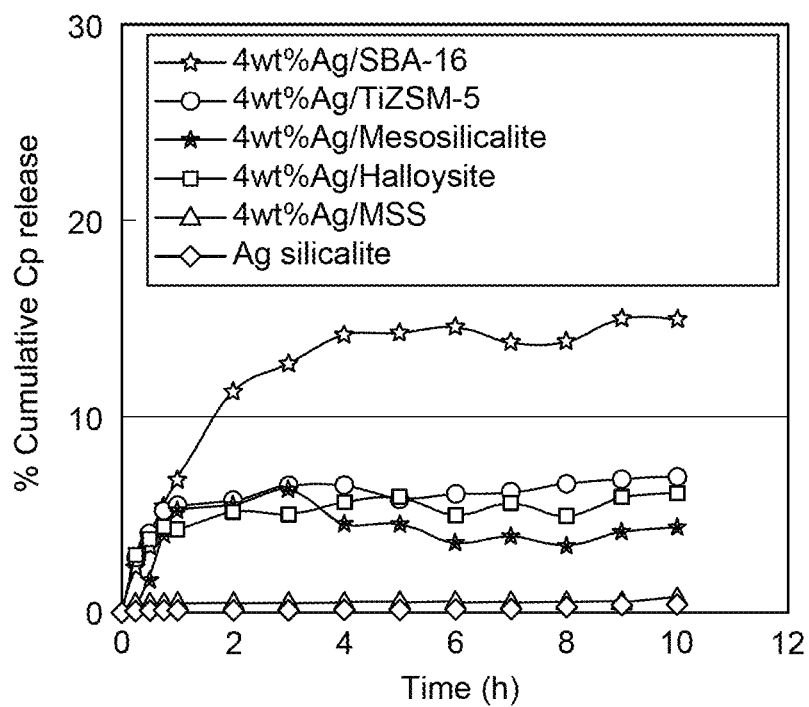
Figure 13C:
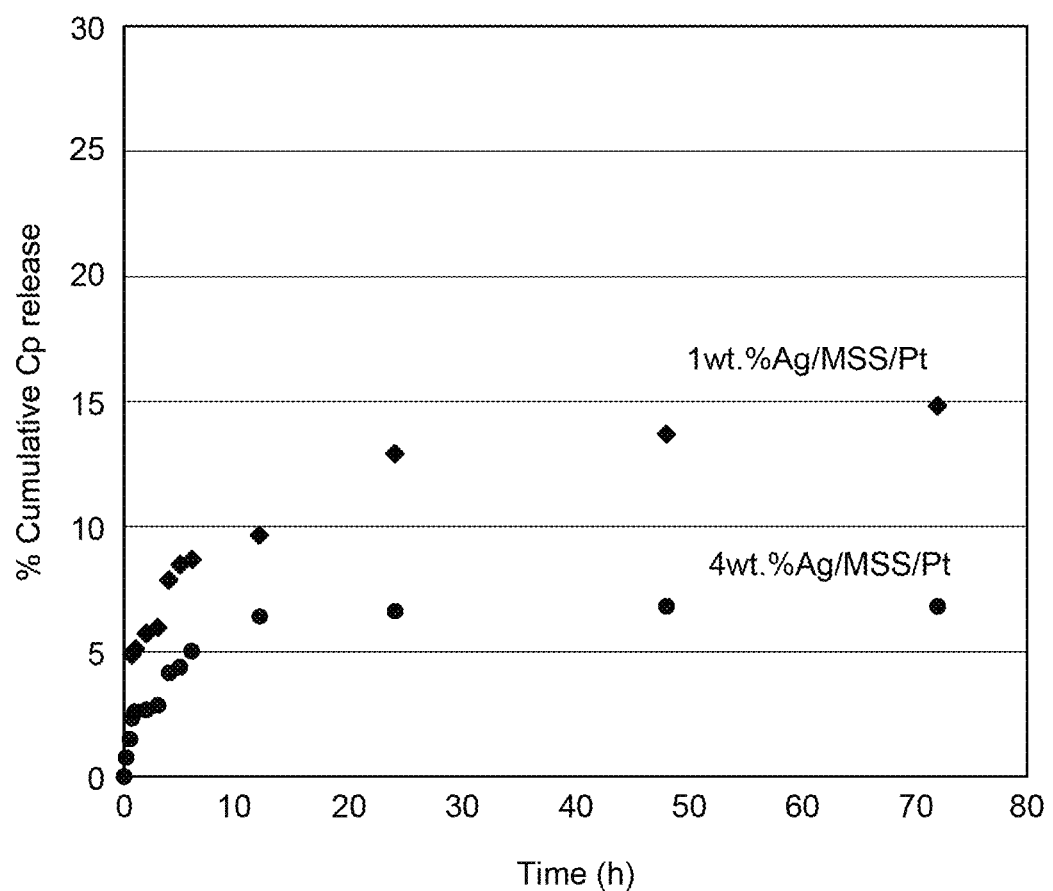
FIG. 13C depicts cisplatin release using a dialysis membrane for 72 hours, respectively, according to certain embodiments.

FIGS. 13A-13B depict in vitro cisplatin release study using an automated Franz cell system for 10 hours, and FIG. 13C depicts cisplatin release using a dialysis membrane for 72 hours. The release ability of cisplatin with increasing Ag loadings over MSS was carried out in a continuous flow system that imitate in vitro cisplatin release. The continuous flow system is more accurate for in vivo conditions with respect to using the dialysis membrane, which is a closed system. In the present condition, sink and saturation levels were negated due to open system (a continuous flow of a buffer solution). Removal and refilling errors were reduced due to semi automation. The release profiles were reproduced with triplicate runs.

In case of cisplatin release (FIG. 13A), the percentage cumulative cisplatin release showed a 1 wt. % Ag/MSS>2 wt. % Ag/MSS>4 wt. % Ag/MSS>6 wt. % Ag/MSS pattern. A quick release of drugs is used for acute diseases. However, slow, and sustained release are beneficial for cancer therapeutics. Such controlled slow release to cancer cells, reduces the toxic effect on normal cells. A cumulative percentage release pattern (FIG. 13A) showed an inverse relation with respect to different weight percentage Ag loading. A quick release of cisplatin occurred at lower Ag loadings (1 wt. % and 2 wt. %) on MSS. However, the release of cisplatin reduces significantly with high Ag loadings (4 wt. % and 6 wt. %). Therefore, 4 wt. % Ag loading was chosen due to sustained release and compared with 4 wt. % Ag loaded on different structured materials. The cisplatin release over different structured silica showed that SBA-16 with cubic shaped pores showed high release (~15%) with short duration between 0-10 h. TiZSM-5 zeolite with micropores, halloysite with nanotube and mesosilicate with mesopores showed an intermediate cisplatin release (3-5%). 4 wt. %/MSS and 6 wt. %/MSS had still remained intact with cisplatin, which confirms the synergistic interaction between Ag and Pt complex (FIG. 13B).

Stability experiments of samples such as 1 wt. % Ag/MSS and 4 wt. % Ag/MSS were studied for the period of 72 h by using the dialysis membrane. 1 wt. % Ag/MSS showed a high cisplatin release reaching of about 15% for 72 h, while 4 wt. % Ag/MSS showed a slow release of about 7% for 72 h. The high release at lower Ag loading and slow sustained release with high Ag correlate with release trend of the Franz cell system (FIG. 13C).

Anticancer Activity Using 1-6 wt. % Ag/MSS/Pt

Figure 14A:
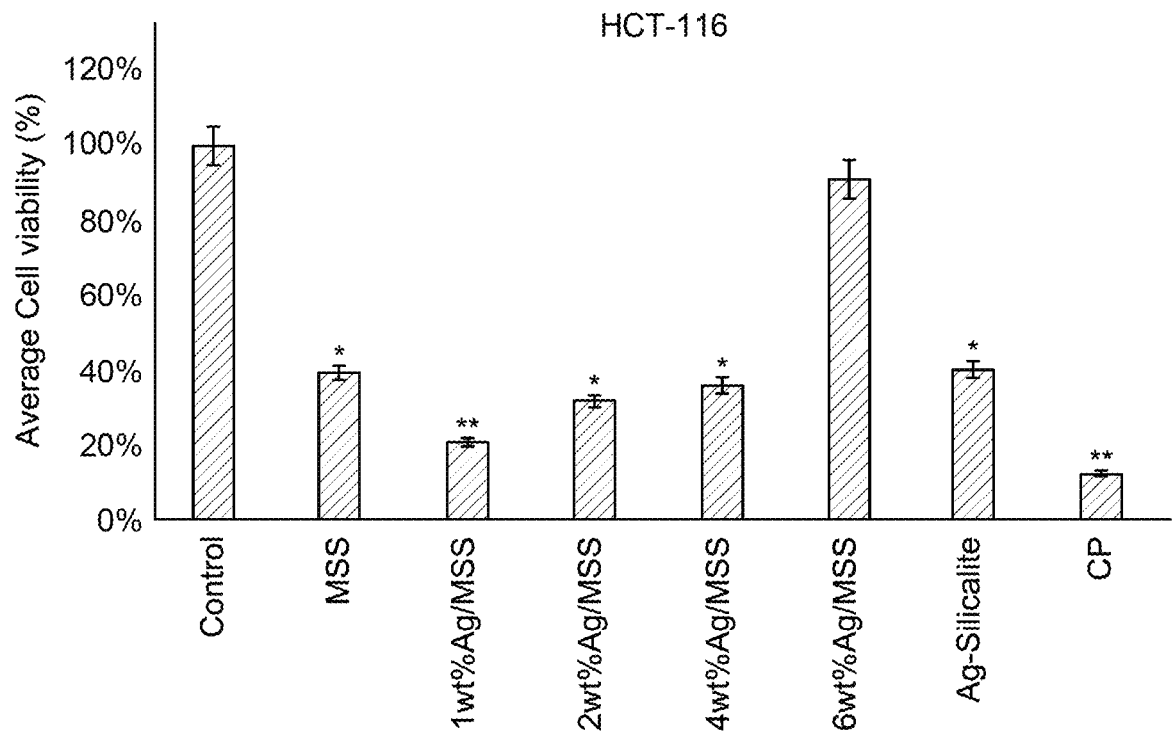
FIG. 14A is a graph depicting the effect of the medicinal nanocomposite on cell viability of human colorectal carcinoma (HCT-116) cells post 48 hours treatment, according to certain embodiments
Figure 14B:
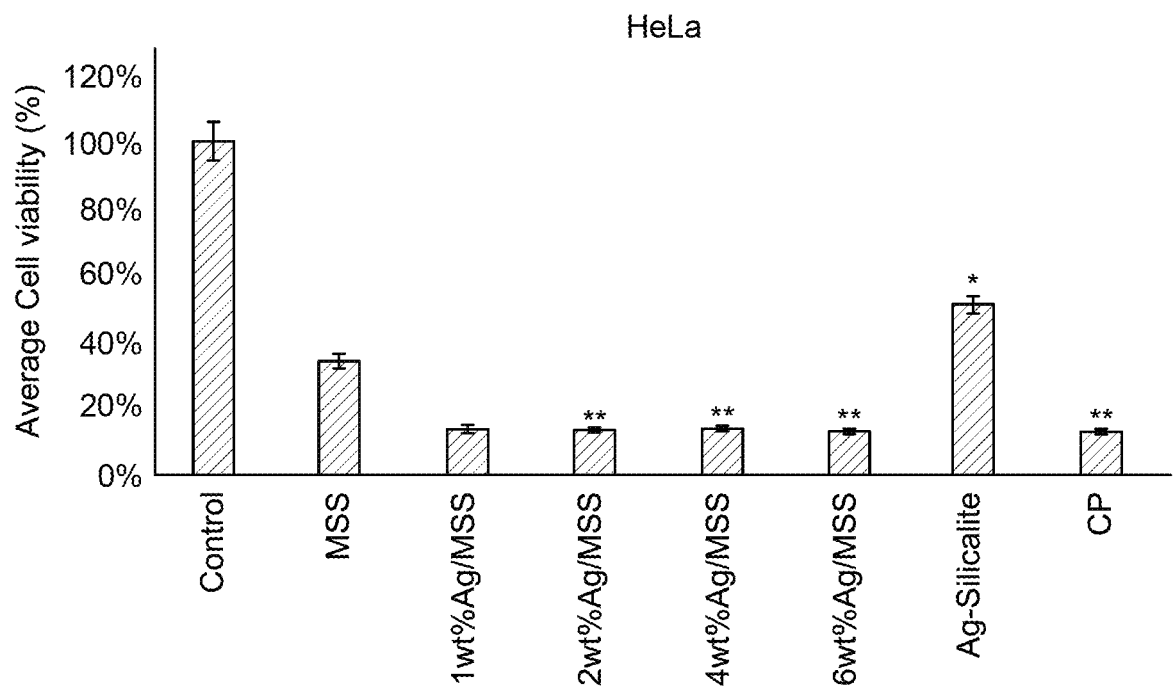
FIG. 14B is a graph depicting the effect of the medicinal nanocomposite on cell viability of human cervical cancer (HeLa) cells post 48 hours treatment, according to certain embodiments.
Figure 14C:
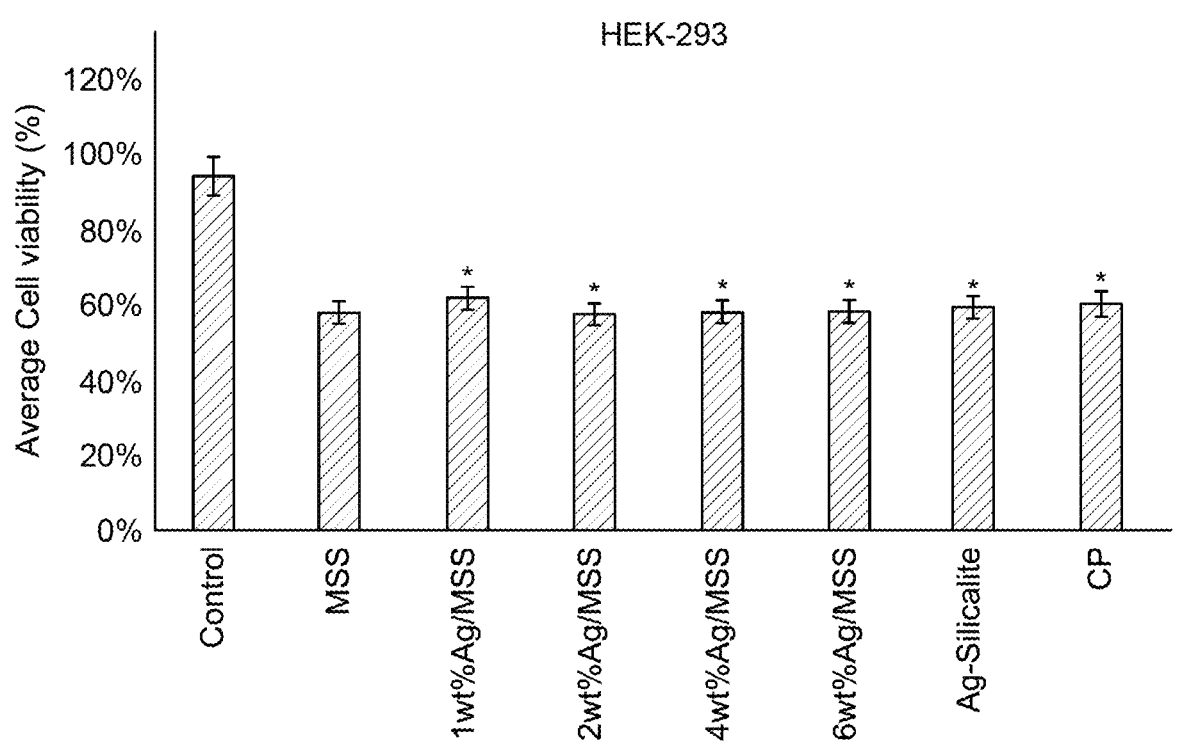
FIG. 14C is a graph depicting the effect of the medicinal nanocomposite on cell viability of embryonic kidney (HEK-293) cells post 48 hours treatment, according to certain embodiments.

Referring to FIGS. 14A-14C, graphs depicting the impact of treatment of nanoparticles on cell viability of HCT-116 cells, HeLa cells, respectively, and normal cells embryonic kidney cells (HEK 293), post 48-hour treatment. The MTT assay was used to evaluate the cell viability. The influence of different weight percentage Ag loadings on MSS at constant cisplatin functionalization over cancer cells such as HeLa and HCT-116 and normal cells embryonic kidney cells (HEK 293) were studied. The normal cells were used to evaluate the cytotoxic effect of nano formulation at the same time HeLa and HCT-116 were used to evaluate the anticancer effect. FIG. 14A shows a significant decrease in the HCT-116 cell viability after the treatments of 1 wt. % Ag/MSS, 2 wt. % Ag/MSS, 4 wt. % Ag/MSS, and 6 wt. % Ag/MSS. However, a significant decrease was not observed in Ag-silicalite. FIG. 14B confirms significant decrease in the HeLa cell viability after the treatments of MSS, 1 wt. % Ag/MSS, 2 wt. % Ag/MSS, 4 wt. % Ag/MSS, 6 wt. % Ag/MSS, and cisplatin, including Ag-silicalite.

The treatments MSS, 1 wt % Ag/MSS, 2 wt % Ag/MSS, 4 wt % Ag/MSS, 6 wt % Ag/MSS, Ag-silicalite and CP showed dose-dependent inhibitory action on cancer cell growth and proliferation.

The inhibitory concentration ($IC_{50}$) for each nano formulation was determined on HCT-116 cells—MSS (23 μg/ml), 1 wt % Ag/MSS (15 μg/ml), 2 wt % Ag/MSS (21 μg/ml), 4 wt % Ag/MSS (26 μg/ml), 6 wt % Ag/MSS (26 μg/ml), and CP (13 μg/ml) on HCT-116 cells. On Hela cells, $IC_{50}$ were MSS (24 μg/ml), 1 wt % Ag/MSS (13 μg/ml), 2 wt % Ag/MSS (14 μg/ml), 4 wt % Ag/MSS (14 μg/ml), 6 wt % Ag/MSS (15 μg/ml), and CP (13 μg/ml).

The impact of MSS, 1 wt. % Ag/MSS, 2 wt. % Ag/MSS, 4 wt. % Ag/MSS, 6 wt. % Ag/MSS, Ag-silicalite and CP on non-cancerous cells (HEK-293) was studied and the results are depicted in FIG. 14C. From the FIG. 14C, it can be observed that the average cell viability was 63% post-treatments of MSS, 1 wt. % Ag/MSS, 2 wt. % Ag/MSS, 4 wt. % Ag/MSS, 6 wt. % Ag/MSS, Ag-silicalite and CP. However, with cancer cells, the cell viability was 35.11% in HCT-116 and 22.44% in HeLa cells post MSS, 1 wt. % Ag/MSS, 2 wt. % Ag/MSS, 4 wt. % Ag/MSS, 6 wt. % Ag/MSS, Ag-silicalite treatments.

Based on the results, it can be observed that the synthesized MSS, 1 wt. % Ag/MSS, 2 wt. % Ag/MSS, 4 wt. % Ag/MSS, 6 wt. % Ag/MSS, Ag-silicalite possess inhibitory effect on HCT-116 and HeLa cells than HEK-293 cells. The cytotoxic impact of nanoparticles post 48 hours of treatment was observed, and the average cell viability for Hela cells, HCT-116 cells and HEK-293 cells was found to be 23.22%, 43.48%, 62.00%, respectively.

Apoptotic Cancer Cell Death

Figure 15D:
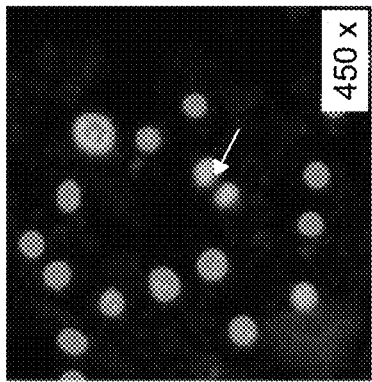
FIGS. 15A-15H are morphological images depicting the impact of the medicinal composite on HCT-116 cells stained with DAPI (4',6-diamidino-2-phenylindole) post 48-hour treatment, according to certain embodiments.
Figure 15H:
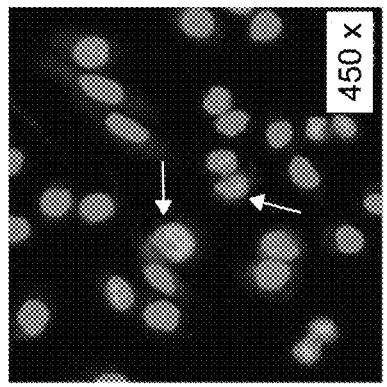
Figure 15C:
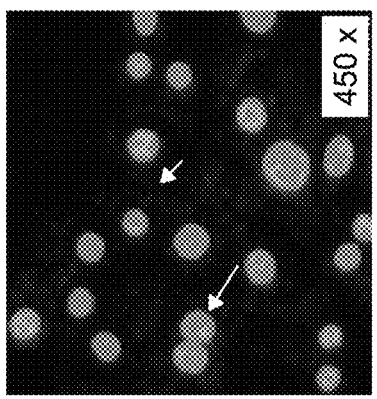
Figure 15G:
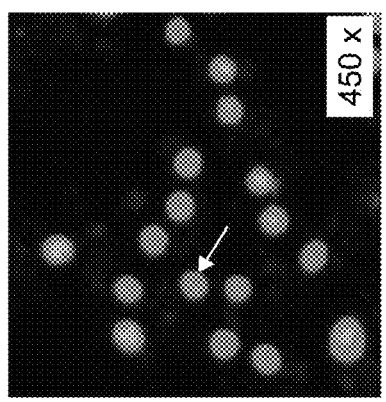
Figure 15B:
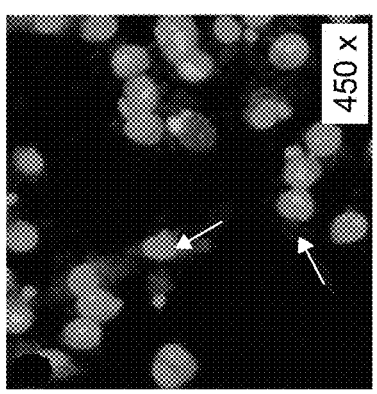
Figure 15F:
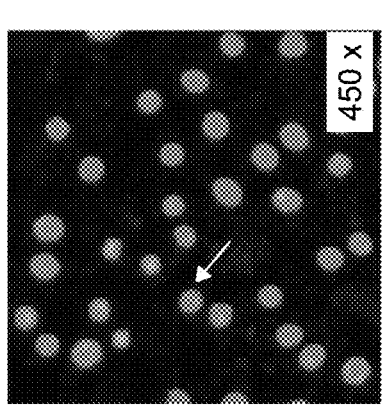
Figure 15A:
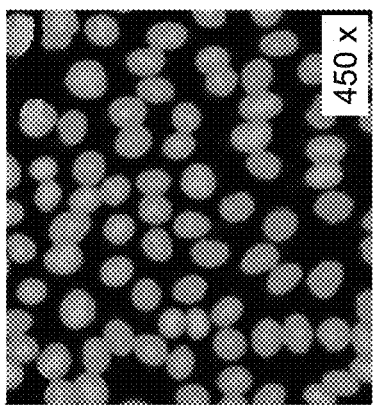
Figure 15E:
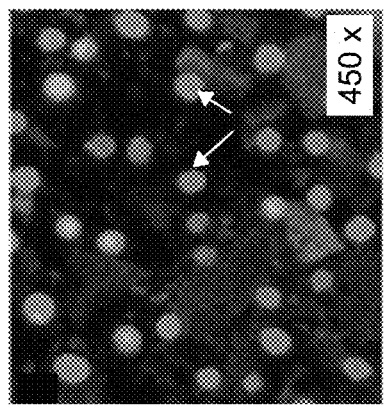
Figure 16:
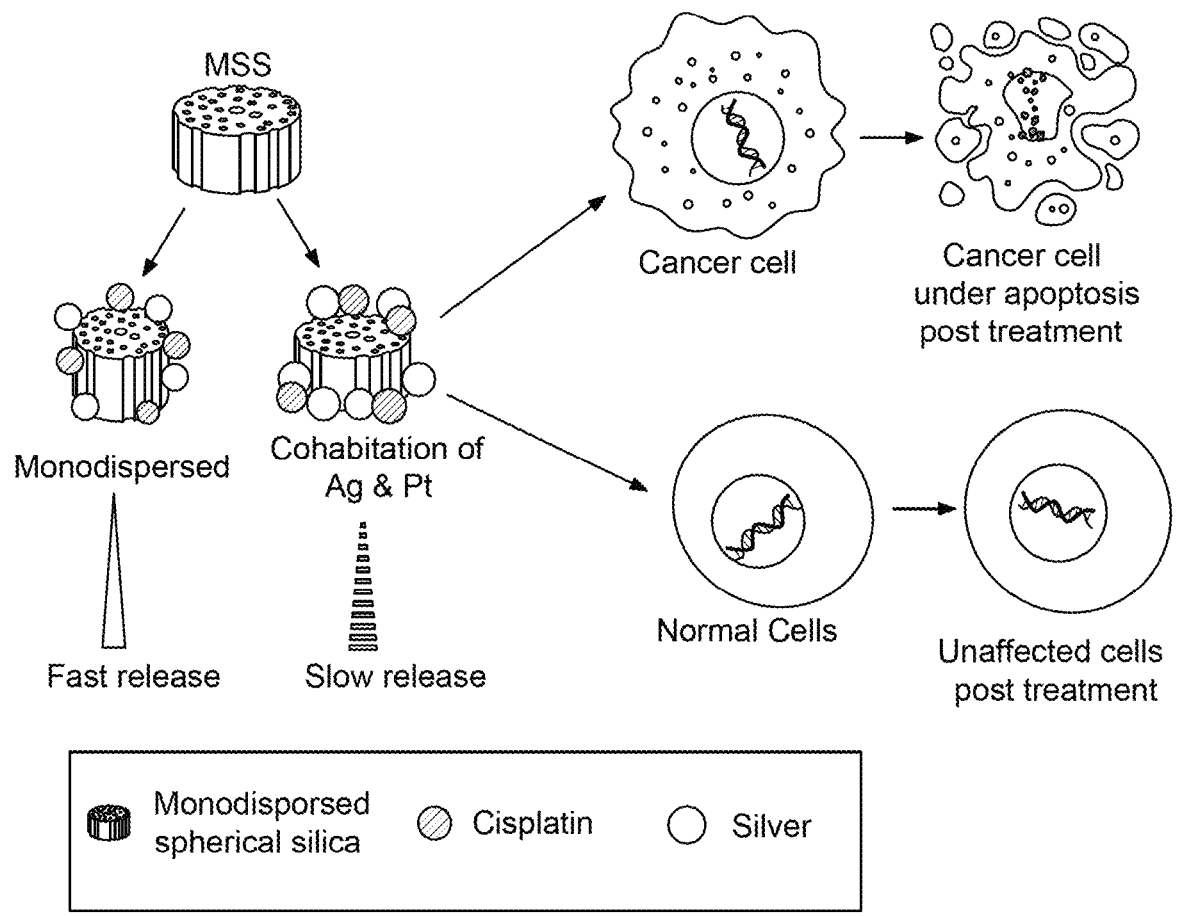
FIG. 16 is an exemplary image of intracellular changes and apoptosis caused by the interaction of the medicinal nanocomposite with the HCT-116 and HeLa cells and normal body cells, according to certain embodiments.

FIGS. 15A-15H show morphological images of HCT-116 cells stained with DAPI post 48-hour treatment. The treatment of MSS, 1 wt. % Ag/MSS, 2 wt. % Ag/MSS, 4 wt. % Ag/MSS, 6 wt. % Ag/MSS, Ag-silicalite and cisplatin caused significant decrease in the number of colon cancer cells, as the number of DAPI stained cells were found to be significantly less in the MSS, 1 wt. % Ag/MSS, 2 wt. % Ag/MSS, 4 wt. % Ag/MSS, 6 wt. % Ag/MSS, Ag-silicalite and cisplatin-treated cells as compared to control cells (FIGS. 15B-15H). The decrease in the cancer cells was due to cell death which are due to programmed cell death or apoptosis (FIG. 16). In contrast, control cells did not show any inhibitory action on the colon cancer cells (FIG. 15A).

Figure 17A:
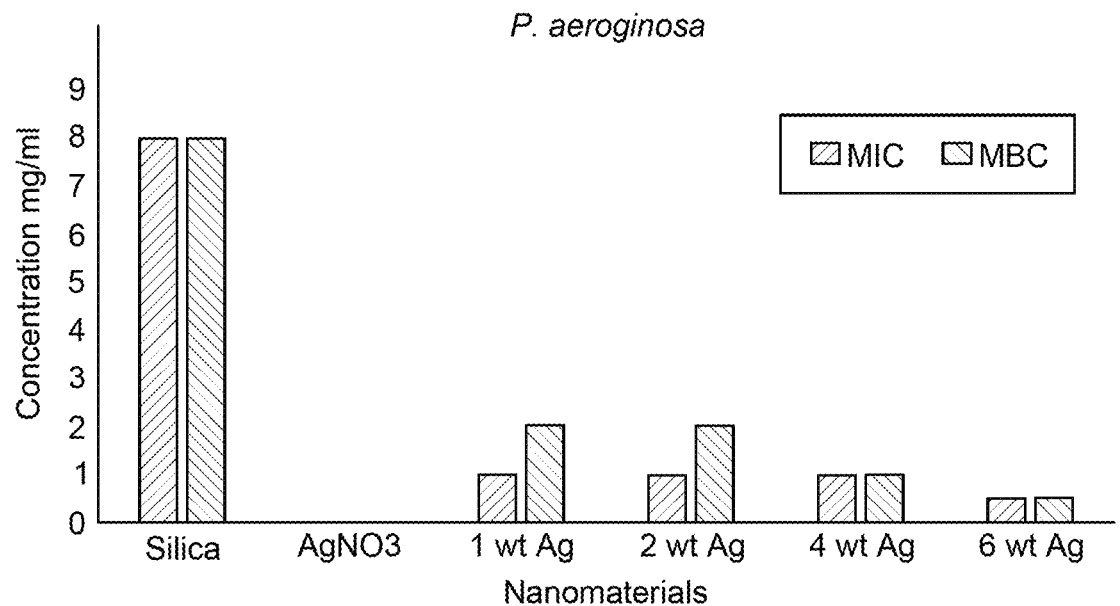
FIGS. 17A-17B are graphical representations of Minimum Inhibitory Concentration (MIC) Minimum Bactericidal Concentration (MBC) values of Ag/MSS, of varying weight percentages, against *Pseudomonas aeruginosa* and *Staphylococcus aureus*, respectively, according to certain embodiments.
Figure 17B:
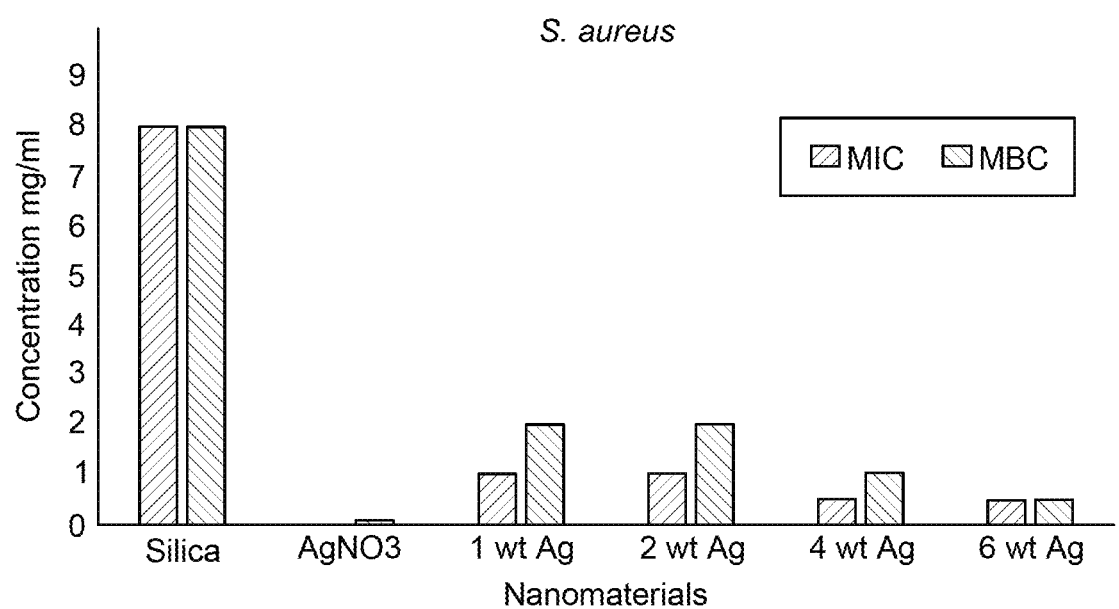

The cubic structured SBA-16, TiZSM-5 (FIGS. 17A-17B), mesosilicalite and halloysite showed higher cisplatin release than 4 wt. % MSS sample. The cell viability study using MTT assay on HCT-116 shows the drug release pattern, where cell viability decreases in the following pattern 1 wt. % Ag/MSS>2 wt. % Ag/MSS>4 wt. % Ag/MSS> and 6 wt. % Ag/MSS. Ag-silicalite, where Ag is incorporated in to a silicalite framework, showed less impact on HCT-116 and HeLa cells. In case of HeLa cells, 1-6 wt. % Ag loaded MSS nano formulation was found to be more sensitive with less cell viability percentage and apparent morphological damage which may be due to cell membrane disruption, nuclear condensation and fragmentation. Ag nanoparticles tend to inhibit cell viability due to oxidative stress. Treatment with normal cells (HEK-293) showed less cytotoxic effect, reflecting the nontoxic effect of nano formulation, irrespective of Ag loadings. Further study with DAPI showed high cell apoptotic effect with cisplatin loading on increased Ag loaded MSS nano formulation. Hence, no relationship occurred with respect to Ag loading and cisplatin release.

Antibacterial Activity Using 1-6 wt. % Ag/MSS

Figure 18A:
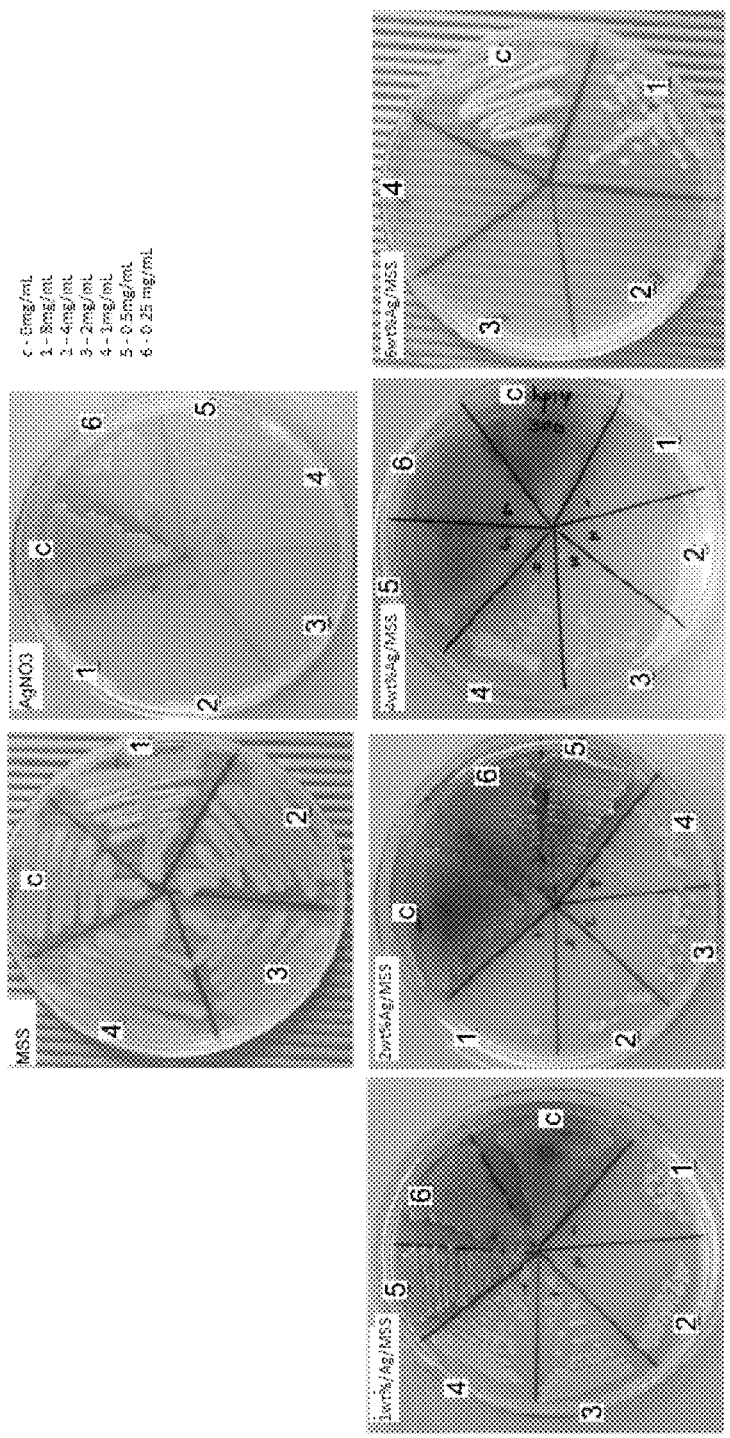
FIGS. 18A-18B are images of agar plates showing the MIC and MBC of an antibacterial composition against *Pseudomonas aeruginosa* and *Staphylococcus aureus*, respectively, according to certain embodiments.
Figure 18B:
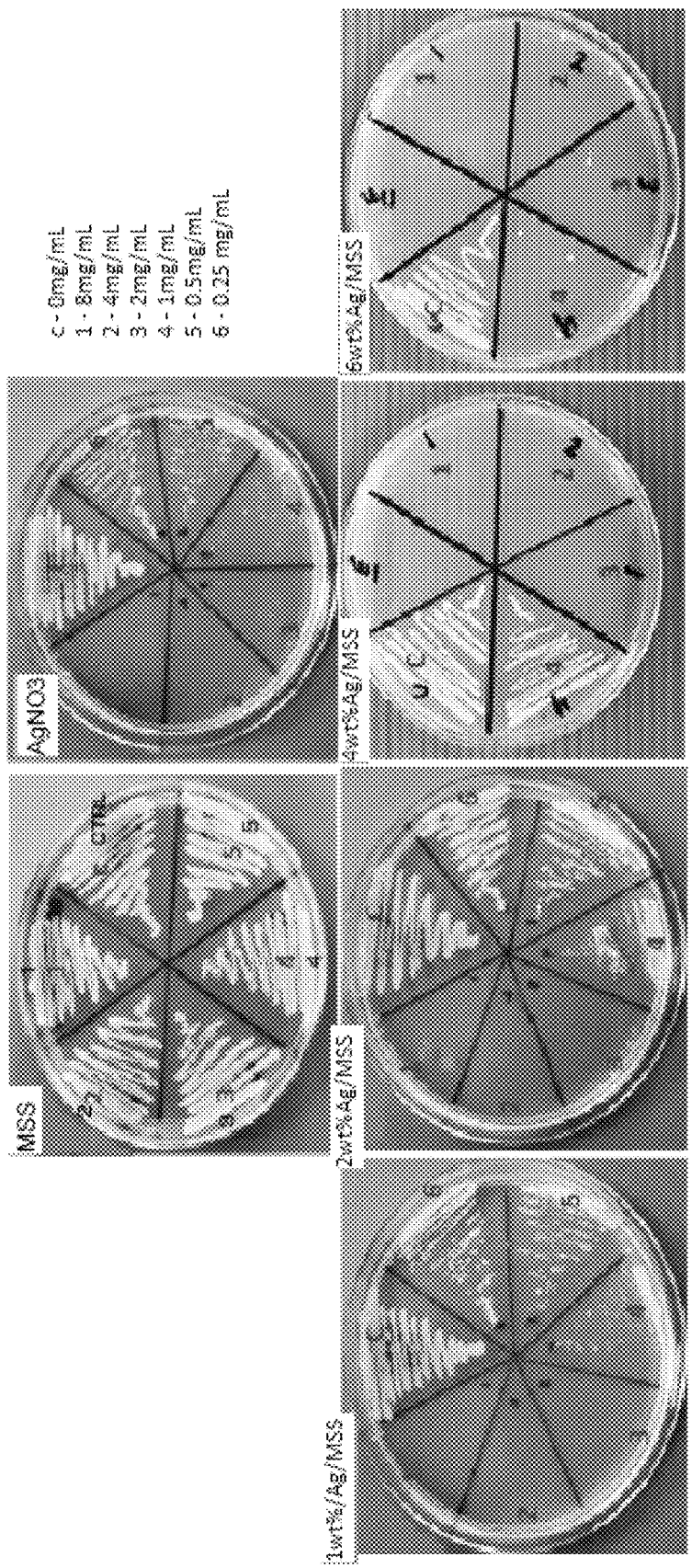

FIGS. 18A-18B refer to graphical representations of the MIC and MBC values for 1-6 wt. % Ag/MSS. The nanomaterials showed appreciable bactericidal activity against *P. aeruginosa* and *S. aureus* except silica which showed no inhibitory action. However, *P. aeruginosa* was seen to be slightly more susceptible compared to *S. aureus*. The minimum concentration of nanomaterial for *P. aeruginosa* and *S. aureus* is presented. The treatments of nanomaterial showed dose-dependent inhibitory action on the bacterial cells. The MSS with different percentage Ag (1 wt. %, 2 wt. %, 4 wt. % and 6 wt. %) exhibited varying impact on the bacterial cells. Growth of *P. aeruginosa* and *S. aureus* were inhibited with the increasing percentage of Ag in MSS.

Figure 19:
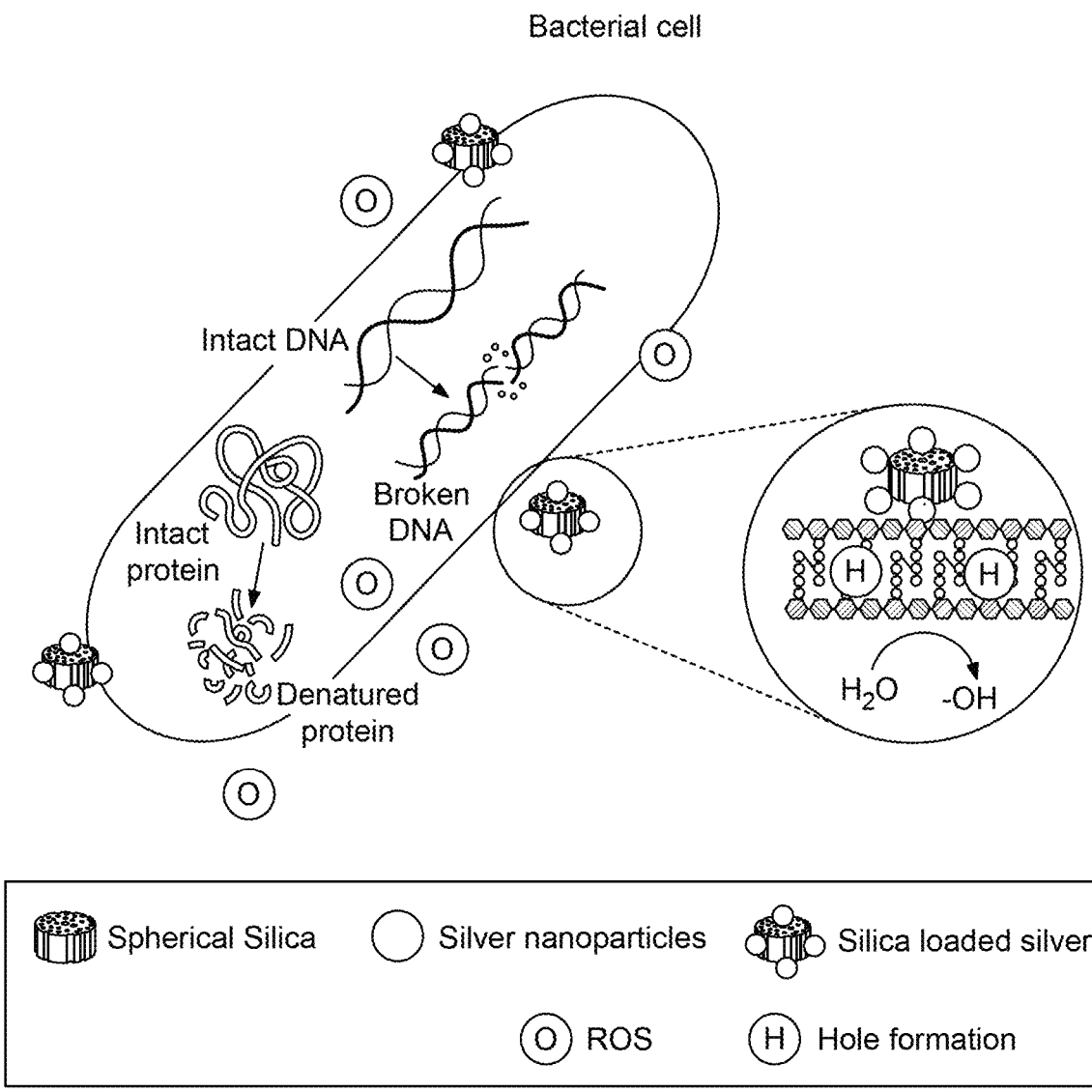
FIG. 19 is an exemplary image of intracellular changes caused by interaction of the antibacterial composition with a bacterial cell surface, according to certain embodiments.

A mass ratio of Ag NPs was evaluated by varying Ag loading in the antibacterial composition. The 6 wt. % Ag loading percentage showed the best efficacy against *P. aeruginosa* and *S. aureus*, which may be due to the dispersion of Ag. Inadequate amount of Ag with only 1 wt. % Ag loading showed the least efficacy. The bactericidal action of pure $AgNO_3$, MSS against *P. aeruginosa*, and *S. aureus*, respectively, are shown in FIGS. 18A and 18B, and 19A and 19B. FIGS. 19A-19B includes (i) the MSS, (ii) $AgNO_3$, (iii) 1 wtAg/MSS, (iv) 2 wtAg/MSS, (v) 4 wtAg/MSS, (vi) 6 wtAg/MSS [1: 8 mg/ml, 2: 4 mg/ml, 3: 2 mg/ml, 4: 1 mg/ml, 5: 0.5 mg/ml, 6: 0.25 mg/ml, c: control; For $AgNO_3$ i.e., (ii): 1: 0.125 mg/ml, 2: 0.0625 mg/ml, 3: 0.031 mg/ml, 4: 0.155 mg/ml, 5: 0.0075 mg/ml, 6: 0.00387 mg/ml, c: control] against *P. aeruginosa*, and *S. aureus*, respectively. The MIC/MBC of all the ratios and $AgNO_3$ showed effectiveness, and that the pristine silica showed no antibacterial activity. The bacterial inhibition was regulated by Ag, most significantly, Ag/MSS nanomaterial confirmed the increased antibacterial activity and stability which could be attributed to the Ag introduced. Using one-way ANOVA, the variation in the antibacterial, using varying concentration Ag loading were found significant ($P<0.001$).

The antibacterial composition is proposed to be attached on the bacterial cell wall and penetrated into the periplasmic space of bacteria cell, generating reactive oxygen species (ROS) which leads to cellular disorganization (FIG. 20). The antibacterial composition may significantly attach to cellular surfaces and produce increased level of ROS, mainly hydroxyl radicals during the interaction of electrons and water under visible light. In the present study, the antibacterial composition may have influenced the dispersion and release of Ag and facilitated the efficient contact with bacterial membranes. The higher dispersion of the nanomaterial may also enhance the surface area, making more ROS production from active sites. The antibacterial composition could release Ag+ ions which interact with bacterial cell structures and damage the bacterial membranes. Ag NPs anchor with the MSS promote the damage caused to the cellular surfaces, which may significantly increase the antibacterial and anticancer activity.

Efficient shape, size and textural (surface area and pore size distributions) characteristics of silica influence a drug solubility, drug release efficacy and bioavailability. The mesoporous silica with particle sizes ranging between 10-100 nm, increases a circulation time and avoid macrophages detection during the circulation. The medicinal nanocomposite provides multifunctional capabilities against microbes, fungal infections, inflammations and cancers. Dual metals such as Ag and Pt possess anticancer and antibacterial activity. Further, Ag NPs anchored with the MSS showed an excellent antibacterial activity against bacterial strains *P. aeruginosa*, and *S. aureus* by promoting damage to the cellular surfaces.

The invention claimed is:

1. A method of forming a medicinal nanocomposite, the method comprising:
   aging a reaction mixture comprising a silver source and carrier particles of a porous silicate material in a first solvent for 4 to 24 hours to form an aged mixture;
   heating the aged mixture to 90 to 150° C. for 2 to 12 hours to form a first product;
   calcining the first product at 350 to 650° C. for 1 to 6 hours to form a second product;
   mixing the second product and a platinum-containing pharmaceutical compound in a second solvent for 2 to 12 hours at −15 to 15° C. to form the medicinal nanocomposite; and
   isolating the medicinal nanocomposite by decanting the second solvent from the medicinal nanocomposite;
   wherein the medicinal nanocomposite comprises:
   80 to 99 wt. % of the carrier particles of the porous silicate material selected from the group consisting of mesoporous silica, silicalite, mesosilicalite, silver-incorporated silicalite, and silver-incorporated mesosilicalite, the carrier particles of the porous silicate material having a pore framework;
   0.5 to 10 wt. % of silver nanoparticles (Ag NPs) dispersed on and in the pore framework, wherein the silver nanoparticles are distinct from silver present in the silver-incorporated silicalite and/or the silver-incorporated mesosilicalite; and
   0.5 to 10 wt. % of the platinum-containing pharmaceutical compound disposed on at least one surface selected from an interior pore surface of the carrier particles, an exterior surface of the carrier particles, and a surface of the silver nanoparticles, wherein the medicinal nanocomposite releases less than 10 mol. % of the platinum-containing pharmaceutical compound after 60 to 84 hours at a pH of 4.5 to 7, based on an initial amount of the platinum-containing pharmaceutical compound present in the medicinal nanocomposite.

2. The method of claim 1, wherein the carrier particles are particles of mesoporous silica which are substantially spherical and have a mean particle size of 50 to 110 nanometer (nm).

3. The method of claim 1, wherein the carrier particles are particles of mesoporous silica which are amorphous by PXRD.

4. The method of claim 1, wherein the carrier particles are porous silicate material selected from the group consisting of silicalite, mesosilicalite, silver-incorporated silicalite, and silver-incorporated mesosilicalite having a mean particle size of 25 to 400 nm.

5. The method of claim 1, wherein the carrier particles are particles of silver-incorporated mesosilicalite having a silicon to silver mole ratio of 10:1 to 150:1.

6. The method of claim 1, wherein the carrier particles are particles of silver-incorporated silicalite having a silicon to silver mole ratio of 10:1 to 150:1.

7. The method of claim 1, wherein the silver nanoparticles are disposed on the interior pore surface of the carrier particles and/or the exterior surface of the carrier particles and have a mean particle size of 5 to 50 nm.

8. The method of claim 1, wherein the silver nanoparticles are crystalline by PXRD.

9. The method of claim 1, wherein the platinum-containing pharmaceutical compound is at least one selected from the group consisting of cisplatin, oxaliplatin, and carboplatin.

10. The method of claim 1, wherein the medicinal nanocomposite has a mean pore size of 15 to 27.5 nm, a mean pore volume of 0.05 to 0.35 cubic centimeter per gram ($cm^3/g$), and a mean surface are of 7.5-75-meter square per gram ($m^2/g$).

11. The method of claim 1, wherein the silver source is silver nitrate.

12. The method of claim 1, wherein the first solvent is water and the second solvent is normal saline solution.

13. The method of claim 1, wherein the porous silicate material is selected from the group consisting of silver-incorporated silicalite and silver-incorporated mesosilicalite, wherein the porous silicate material is prepared by:

adding a suspension of colloidal silica in the first solvent to a basic solution comprising 2 to 3 M hydroxide base to form a raw silicate solution;

aging the raw silicate solution for 1 to 30 minutes to form an aged silicate solution;

adding the silver source to the aged silicate solution to form a first reaction mixture;

aging the first reaction mixture to form an aged reaction mixture;

adding a template selected from the group consisting of tetrapropyl ammonium hydroxide and cetyltrimethyl ammonium bromide to form a templated solution;

stirring the templated solution for 0.5 to 3 hours to form a second reaction mixture;

hydrothermally treating the second reaction mixture at 125 to 195° C. for 24 to 120 hours to form a first precipitate; and calcining the first precipitate at 400 to 750° C. for 2 to 12 hours to form the porous silicate material.

14. The method of claim 13, wherein the template is tetrapropyl ammonium hydroxide and the porous silicate material is silver-incorporated silicalite.

15. The method of claim 13, wherein the template is cetyltrimethyl ammonium bromide, and the porous silicate material is silver-incorporated mesosilicalite.

\* \* \* \* \*